(12) United States Patent
Szyperski et al.

(10) Patent No.: US 7,586,306 B2
(45) Date of Patent: Sep. 8, 2009

(54) SIMULTANEOUSLY CYCLED NMR SPECTROSCOPY

(75) Inventors: Thomas Szyperski, Amhert, NY (US); David Parish, Buffalo, NY (US)

(73) Assignee: Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 12/181,857

(22) Filed: Jul. 29, 2008

(65) Prior Publication Data

US 2009/0033326 A1 Feb. 5, 2009

Related U.S. Application Data

(60) Provisional application No. 61/026,894, filed on Feb. 7, 2008, provisional application No. 60/952,666, filed on Jul. 30, 2007.

(51) Int. Cl.
*G01V 3/00* (2006.01)
(52) U.S. Cl. ..................... 324/309; 324/307
(58) Field of Classification Search ......... 324/300–322; 600/407–445
See application file for complete search history.

(56) References Cited

U.S. PATENT DOCUMENTS

| 5,162,723 | A | * | 11/1992 | Marzalek et al. ......... 324/76.19 |
| 6,831,459 | B2 | | 12/2004 | Szyperski et al. |
| 6,873,153 | B2 | * | 3/2005 | Frydman ................... 324/307 |
| 7,141,432 | B2 | | 11/2006 | Szyperski |
| 7,271,588 | B2 | * | 9/2007 | Frydman ................... 324/318 |
| 7,365,539 | B2 | | 4/2008 | Szyperski et al. |
| 7,396,685 | B2 | | 7/2008 | Szyperski et al. |
| 7,408,346 | B2 | | 8/2008 | Szyperski et al. |
| 7,425,828 | B2 | * | 9/2008 | Garwood et al. ............ 324/310 |
| 2006/0111846 | A1 | | 5/2006 | Szyperski et al. |
| 2009/0009166 | A1 | | 1/2009 | Szyperski et al. |

FOREIGN PATENT DOCUMENTS

| WO | 0203081 A2 | 1/2002 |
| WO | 2004007016 A2 | 1/2004 |
| WO | 2004011909 A2 | 2/2004 |
| WO | 2007002464 A2 | 1/2007 |
| WO | 2009018276 A1 | 2/2009 |

OTHER PUBLICATIONS

International Search Report for International Patent Application No. PCT/US08/71475 (Oct. 20, 2008).
Parish et al., "Simultaneously Cycled NMR Spectroscopy," J. Am. Chem. Soc. 130:4925-4933 (2008).

(Continued)

*Primary Examiner*—Brij B Shrivastav
(74) *Attorney, Agent, or Firm*—Nixon Peabody LLP

(57) ABSTRACT

The present invention relates to a method for simultaneously conducting multiple steps of a cycle of a nuclear magnetic resonance (NMR) experiment without the use of pulsed magnetic field gradients during signal detection in which one or more spatially selective radiofrequency pulses are applied to a sample under conditions effective to simultaneously spatially distribute the radiofrequency power associated with each of the cycle steps to a plurality of spatially discrete sections within the sample such that each section executes an individual step of the cycle and the resultant NMR signals from each of the cycle steps are produced simultaneously.

20 Claims, 12 Drawing Sheets

OTHER PUBLICATIONS

Frydman et al., "The Acqusition of Multidimensional NMR Spectra Within a Single Scan," Proc. Natl. Acad. Sci. USA 99:15858-15862 (2002).

Frydman, et al., "Principles and Features of Single-Scan Two-Dimensional NMR Spectroscopy," J. Am. Chem. Soc. 125:9204-9217 (2003).

Shrot et al., "Single-Scan NMR Spectroscopy at Arbitrary Dimensions," J. Am. Chem. Soc. 125:11385-11396 (2003).

Tal et al., "Spatial Encoding and the Acquisition of High Definition MR Images in Inhomogeneous Magnetic Fields," J. Magn. Reson. 181:179-194 (2006).

Bhattacharyya et al., "A Fast Method for the Measurement of Long Spin-Lattice Relaxation Times by Single Scan Inversion Recovery Experiment," Chem. Phys. Lett. 383:99-103 (2004).

Loening et al., "Single-scan Longitudinal Relaxation Measurements in High-Resolution NMR Spectroscopy," J. Magn. Reson. 164:321-328 (2003).

Murali et al., "Spectral Unraveling by Space-Selective Hadamard Spectroscopy." J. Magn. Reson. 179:182-189 (2006).

Mishkovsky et al., "Spatially Encoded Strategies in the Execution of Biomolecular-oriented 3D NMR Experiments." J. Biomol. NMR 39:291-301 (2007).

D. Parish, "Development and Application of Methodology for Rapid NMR Data Collection and Protein Structure Determination," Doctor of Philosophy Dissertation, Department of Structural Biology, State University of New York at Buffalo (Apr. 11, 2008).

* cited by examiner

SIMULTANEOUSLY CYCLED NMR SPECTROSCOPY

This application claims the benefit of U.S. Provisional Patent Application Ser. No. 60/952,666, filed Jul. 30, 2007 and U.S. Provisional Patent Application Ser. No. 61/026,894, filed Feb. 7, 2008, which are hereby incorporated by reference in their entirety.

This invention was made with government support under grant number MCB-0416899 awarded by the National Science Foundation. The government has certain rights in this invention.

FIELD OF THE INVENTION

The present invention relates to a method for simultaneously conducting multiple steps of a cycle of a nuclear magnetic resonance (NMR) experiment without the use of pulsed magnetic field gradients during signal detection.

BACKGROUND OF THE INVENTION

Fourier Transform (FT) nuclear magnetic resonance (NMR) spectroscopy (Ernst et al., *Principles of Nuclear Magnetic Resonance in One and Two Dimensions*, Oxford Univ. Press: Oxford (1987)) is one of the most widely used analytical tools in science and engineering (Jacobsen, *NMR Spectroscopy Explained*; Wiley: New York (2007)). FT NMR experiments rely on acquiring 'free induction decays' (FIDs) which, after FT, yield the desired frequency domain spectra. Quite generally, more than a single FID has to be recorded for a given NMR experiment in order to suppress spectral artifacts and/or to implement multi-dimensional data acquisition based on sampling of indirect evolution time periods and coherence pathway selection. Particularly when considering the unprecedented sensitivity of spectrometers equipped with cryogenic probes, one nowadays routinely faces the situation that the NMR experiment time is dictated by the number of FIDs required to record a distinct type of spectrum (with sufficient resolution in indirect dimensions), and not by sensitivity limitations which require signal averaging beyond the need for radio-frequency phase cycling and indirect time domain sampling. (Szyperski et al., *Proc. Natl. Acad. Sci. U.S.A.*, 99:8009-8014 (2002)). To best capitalize on costly NMR hardware, one evidently prefers 'sensitivity limited' data acquisition (Szyperski et al., *Proc. Natl. Acad. Sci. U.S.A.*, 99:8009-8014 (2002)) in which the number of FIDs, i.e., the measurement time, is chosen such that the resulting signal-to-noise (S/N) ratios are adjusted to a level ensuring reliable data interpretation while avoiding unnecessarily high S/N ratios.

NMR approaches were thus developed to accelerate NMR data acquisition (Atreya et al., *Methods Enzymol.*, 394:78-108 (2005)). Many innovations emerged in the field of biological NMR spectroscopy (Cavanagh et al., *Protein NMR Spectroscopy*, Academic Press: San Diego (2007)) where stable isotope ($^{13}C/^{15}N$) labeled biological macromolecules are studied. The isotope labeling enables one to efficiently record three-dimensional (3D) or four-dimensional (4D) $^{13}C/^{15}N$-resolved spectra. In turn, the high spectral dimensionality implies high sampling demand and long minimal measurement times, which creates an urgent demand for rapid data acquisition techniques. Widely used biological NMR techniques include: (i) Reduced-dimensionality (RD) NMR (Szyperski et al., *J. Am. Chem. Soc.*, 115:9307-9308 (1993); Brutscher et al., *J. Magn. Reson. Ser. B*, 105:77-82 (1994); Szyperski et al., *J. Biomol. NMR*, 11:387-405 (1998); Szyperski et al., *Proc. Natl. Acad. Sci. U.S.A.*, 99:8009-8014 (2002)), (ii) its generalization, G-matrix FT (GFT) projection NMR (Kim et al., *J. Am. Chem. Soc.*, 125:1385-1393 (2003); Atreya et al., *Proc. Natl. Acad. Sci. U.S.A.*, 101:9642-9647 (2004); Kim et al., *J. Biomol. NMR*, 28:117-130 (2004); Xia et al., *J. Biomol. NMR*, 29:467-474 (2004); Atreya et al., *J. Am. Chem. Soc.*, 127:4554-4555 (2005); Eletsky et al., *J. Am. Chem. Soc.*, 127:14578-14579 (2005); Yang et al., *J. Am. Chem. Soc.*, 127:9085-9099 (2005); Szyperski et al., *Magn. Reson. Chem.*, 44:51-60 (2006); Atreya et al., *J. Am. Chem. Soc.*, 129:680-692 (2007); Xia et al., *J. Magn. Resoni.*, 190:142-148 (2008)) and the techniques PR NMR (Kupce et al., *J. Am. Chem. Soc.*, 126:6429-40 (2004)), APSY (Hiller et al., *Proc. Natl. Acad. Sci. U.S.A.*, 102:10876-10881 (2005)), and Hi-Fi NMR (Eghbalnia et al., *J. Am. Chem. Soc.*, 127: 12528-12536 (2005)) which are based on GFT NMR data collection, and (iii) Covariance NMR spectroscopy (Bruschweiler, *J. Chem. Phys.*, 121:409-414 (2004); Bruschweiler et al., *J. Chem. Phys.*, 120:5253-5260 (2004); Zhang et al., *J. Am. Chem. Soc.*, 126:13180-13181 (2004); Chen et al., *J. Am. Chem. Soc.*, 128:15564-15565 (2006)). Longitudinal relaxation optimization (Pervushin et al., *J. Am. Chem. Soc.*, 124:12898-12902 (2002); Deschamps et al., *J. Magn. Reson.*, 178:206-211 (2006)) can further accelerate data acquisition for experiments based on initial excitation and detection of polypeptide backbone amide proton (Atreya et al., *Proc. Natl. Acad. Sci. U.S.A.*, 101:9642-9647 (2004); Schanda et al., *J. Am. Chem. Soc.*, 128:9042-9043 (2006); Gal et al., *J. Am. Chem. Soc.*, 129:1372-1377 (2007)) or aromatic proton magnetization (Eletsky et al., *J. Am. Chem. Soc.*, 127:14578-14579 (2005)). Valuable other approaches were developed and thus far primarily applied for smaller molecules, e.g. Hadamard NMR spectroscopy (Bircher et al., *J. Magn. Reson.*, 89:146-152 (1990); Blechta et al., *Chem. Phys. Lett.*, 215:341-346 (1993)) and Ultrafast NMR (Frydman et al., *Proc. Natl. Acad. Sci. U.S.A.*, 99:15858-15862 (2002); Frydman et al., *J. Am. Chem. Soc.*, 125:9204-9217 (2003); Shrot et al., *J. Chem. Phys.*, 125:204507(1-12) (2006); Mishkovsky et al., *J. Biomol. NMR*, 39:291-301 (2007)).

Ultrafast NMR is the only technique that allows one to record multidimensional spectra with a single scan. It is based on (i) spatiotemporal encoding of indirect chemical shift evolution followed by (ii) repetitive decoding and re-encoding during evolution of chemical shifts in the direct dimension. Step (i) requires the application of a train of spatially selective excitation pulses, each consisting of a shaped radiofrequency pulse in conjunction with a pulsed field gradient (PFG). This ensures that only a fraction of the sample, for example, a 'section' is excited. Step (ii) is based on the employment of a train of PFGs with alternating signs ('readout PFGs') during signal detection, which poses high demands on the spectrometer hardware. Even if the significant loss of sensitivity associated with the application of readout PFGs can be reduced using a single readout PFG of constant strength (Shrot et al., *J. Chem. Phys.*, 125:204507(1-12) (2006)), the requirement to incorporate these PFGs represents a major limitation of Ultrafast NMR.

In another vein, Loening et al. (Loening et al., *J. Magn. Reson.*, 164:321-328 (2003)) and Bhattacharyya and Kumar (Bhattacharyya et al., *Chem. Phys. Lett.*, 383:99-103 (2004)) have employed spatially selective excitation to speed up nuclear spin relaxation measurements. In these experiments, separation of signals arising from spatially different parts of the sample is accomplished either by 'time-staggered' acquisition or by use of readout PFGs. Spatially selective excitation has also been applied to high resolution NMR for the suppression of zero-quantum coherence (Thrippleton et al.,

*Angew. Chem. Intl. Ed. Engl.*, 42:3938-3941 (2003); Cano et al., *J. Magn. Reson.*, 167:291-297 (2004)).

For a large number of widely used, often 2D [$^1$H,$^1$H] NMR experiments, it is the cycling of radiofrequency pulse phases or radiofrequency pulse flip-angles for coherence selection and/or artifact suppression (Ernst et al., *Principles of Nuclear Magnetic Resonance in One and Two Dimensions*, Oxford Univ. Press, Oxford (1987)) which dictates, besides the sampling of indirect evolution periods, minimal measurement times: an n-step cycle implies that (at least) n FIDs have to be acquired and added.

Consequently, there is a genuine need for methods which allow a phase, flip angle, or pulsed field gradient strength cycle to be performed simultaneously rather than sequentially. The present invention is directed to overcoming these and other deficiencies in the art.

SUMMARY OF THE INVENTION

The present invention relates to a method for simultaneously conducting multiple steps of a cycle of a nuclear magnetic resonance (NMR) experiment without applying pulsed magnetic field gradients during signal acquisition. The method involves providing a sample and designing the cycle so that the receiver phase for each step of the cycle of the NMR experiment is the same. Then, one or more spatially selective radiofrequency pulses are applied to the sample under conditions effective to simultaneously spatially distribute the radiofrequency power associated with each of the cycle steps to a plurality of spatially discrete sections within the sample such that each section executes an individual step of the cycle and the resultant NMR signals from each of the cycle steps are produced simultaneously. Next, the method involves acquiring NMR signals generated from said applying without applying pulsed magnetic field gradients during signal acquisition.

Simultaneously cycled (SC) NMR in accordance with the present invention enables one to simultaneously execute cycles of radiofrequency pulse flip angles, radiofrequency pulse phases, or PFG strengths. In particular, spatially selective radiofrequency pulses are applied as composite pulses. The minimal measurement time of an NMR experiment performed with an n-step cycle is thus reduced n-fold, indicating that SC NMR represents a valuable addition to the arsenal of approaches for tackling the NMR sampling problem (Atreya et al., *Methods Enzymol.*, 394:78-108 (2005), which is hereby incorporated by reference in its entirety). Since read-out PFGs and their associated increased sampling rate are avoided, a largely increased intrinsic sensitivity is achieved when compared with Ultrafast NMR (Frydman et al., *J. Am. Chem. Soc.*, 125:9204-9217 (2003), which is hereby incorporated by reference in its entirety). For the same reason, SC NMR offers the same line-shapes and thus the same high resolution in the detected dimension as conventional experiments, whereas Ultrafast NMR may suffer from compromised spectral widths, resolution, and linewidth due to finite PFG strength and PFG drooping (Frydman et al., *J. Am. Chem. Soc.*, 125:9204-9217 (2003), which is hereby incorporated by reference in its entirety). Furthermore, careful design of selective radiofrequency pulses results in an intrinsic sensitivity for SC NMR experiments with two or three selective radiofrequency pulses, which is quite comparable to the sensitivity of their conventional congeners. Finally, the acquisition speed of SC NMR can be further increased by sparse data sampling (Schmieder et al, *J. Biomol. NMR*, 3:569-576 (1993); Hoch et al., *NMR Data Processing*; Wiley-Liss: New York (1996); Jaravine et al., *Nature Methods*, 3:605-607 (2006), which are hereby incorporated by reference in their entirety) or covariance NMR processing (Bruschweiler, *J. Chem. Phys.*, 121:409-414 (2004), which is hereby incorporated by reference in its entirety). Taken together, SC NMR promises to impact NMR data acquisition in various areas of research, including chemistry, engineering, and biology.

BRIEF DESCRIPTION OF THE DRAWINGS

In FIG. 2A, the temporal shape of the 3-lobed sinc pulse constructed from $S(t)=\sin(\pi t)/(\pi t)$ for $-3<t<3$, is shown. The excitation profile can be approximated by a Fourier transform (FIG. 2B) which shows the expected rectangular profile with a full spectral width at half max (FWHM) of 60 kHz. FIG. 2C shows the experimentally determined spatial excitation profile (radiofrequency excitation as a function of position, z, within the sample) which is observed by applying a readout PFG during acquisition and Fourier transforming the resultant PFG refocused echo. The real and imaginary parts are displayed in dashed and solid lines, respectively.

In FIG. 3A, a 12-step cycle is employed for the flip-angle of the second radiofrequency pulse along with the receiver phase according to values provided in Table 1. In FIG. 3B, a 12-step cycle is employed for the radiofrequency pulse phases along with the receiver phases according to the values of Table 1. In FIG. 3C, a 3-step cycle is employed for the strength of PFG2, which is set to three times the strength of PFG1 for two steps, and to twice the strength of PFG1 for one step. For the current study, the duration and amplitude of PFG1 are 300 μs and 20 G/cm, respectively.

FIG. 4A: SFC E.COSY. PFG1, 270 μs, 47 G/cm; PFG2, 270 μs, −47 G/cm; PFG3, 135 μs, 50 G/cm. FIG. 4B: SPC E.COSY. PFG1, 270 μs, 47 G/cm; PFG2, 270 μs, −47 G/cm; PFG3, 270 μs, 47 G/cm; PFG4, 150 μs, 45 G/cm. FIG. 4C: SGC E.COSY. PFG1, 100 μs, 22.55 G/cm; PFG2, 120 μs, 18.8 G/cm; PFG3, 125 μs, 35 G/cm.

FIGS. 5A-B: simultaneous flip angle cycling (SFC)—first radiofrequency pulse, temporal waveform and excitation profile (a solid line represents $M_x$ and a dashed line represents $M_y$), respectively. FIGS. 5C-D: SFC—second radiofrequency pulse. FIGS. 5E-F: simultaneous phase cycling (SPC)—first radiofrequency pulse. The second radiofrequency pulse shows a profile that is reverse to the one of the first radiofrequency pulse. FIGS. 5G-H: SPC—third radiofrequency pulse. FIGS. 5I-J: simultaneous gradient strength cycling (SGC)—selective re-phasing pulse.

FIG. 6A: QSIM (Helgstrand et al., *J. Biomol. NMR*, 30:71-80 (2004), which is hereby incorporated by reference in its entirety) simulation; FIG. 6B: phase cycled conventional E.COSY (see FIG. 3B); FIG. 6C: PFG coherence selected conventional E.COSY (see FIG. 3C); FIG. 6D: SFC E.COSY (see FIG. 4A); FIG. 6E: SPC E.COSY (see FIG. 4B); and FIG. 6F: SGC E.COSY (see FIG. 4C).

DETAILED DESCRIPTION OF THE INVENTION

Figure 1:
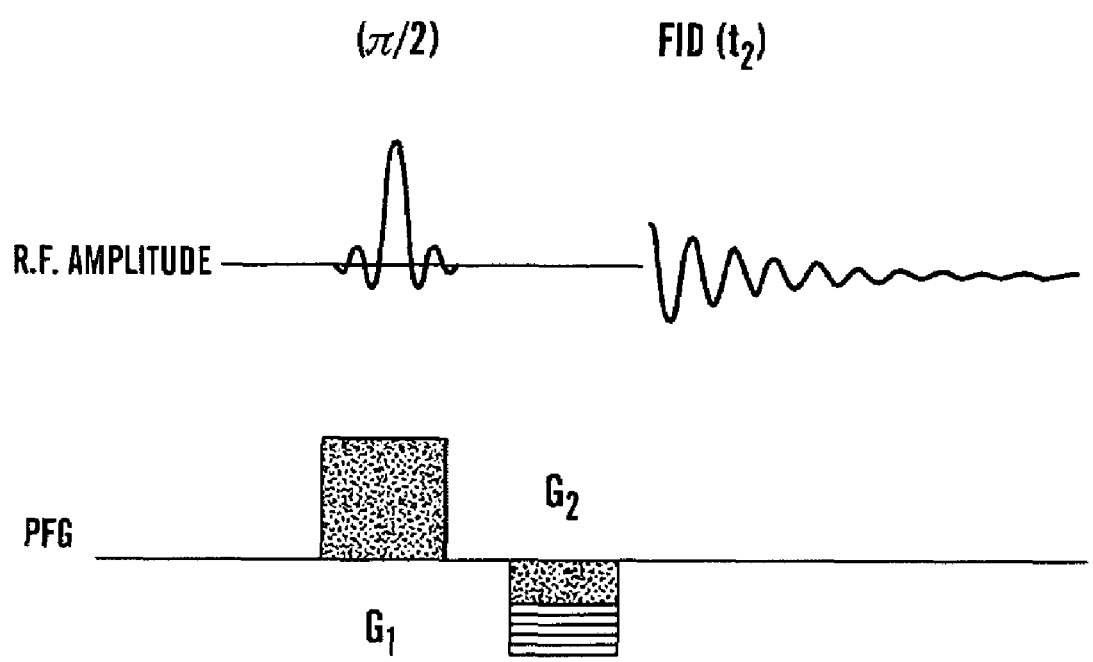
FIG. 1 shows a pulse sequence for spatially selective excitation. A selection pulsed field gradient, PFG1, is applied concurrently with a selective radiofrequency pulse. The finite duration of PFG1 causes dephasing (a phase error that is linear with position in the sample). The strength of PFG2 is about half of the strength of PFG1 and is experimentally adjusted to rephase or eliminate this dephasing.

The present invention relates to a method for simultaneously conducting multiple steps of a cycle of a nuclear magnetic resonance (NMR) experiment without applying pulsed magnetic field gradients during signal acquisition. The method involves providing a sample and designing the cycle so that the receiver phase for each step of the cycle of the NMR experiment is the same. Then, one or more spatially selective radiofrequency pulses are applied to the sample under conditions effective to simultaneously spatially distribute the radiofrequency power associated with each of the cycle steps to a plurality of spatially discrete sections within the sample such that each section executes an individual step of the cycle and the resultant NMR signals from each of the cycle steps are produced simultaneously. Next, the method involves acquiring the NMR signals generated from said applying without applying pulsed magnetic field gradients during signal acquisition.

Simultaneous cycling in accordance with the present invention uses spatially selective excitation to partition NMR experiments into specific physical regions or "sections" of the sample. For spatially non-overlapping sections, separate, shaped radiofrequency excitation pulses that individually excite distinct sections within the sample can be added together to form "composite" radiofrequency pulses (i.e., if they have non-overlapping spatial excitation profiles, multiple shaped radiofrequency pulses ("component pulses") can be added together to form a "composite pulse" that simultaneously excites multiple regions or "sections" of the sample). The section corresponding to each component pulse can be spatially offset relative to the center of the sample by modulating the temporal shape for that component with a sinusoid of appropriate frequency.

Thus, in accordance with the present invention, the one or more spatially selective radiofrequency pulses comprise a composite radiofrequency pulse, as described above, applied simultaneously with pulsed field gradients to encode spatial selectivity. The composite radiofrequency pulses comprise a plurality of component radiofrequency pulses which individually excite distinct sections within the sample. In particular, the spatially selective radiofrequency pulses act upon a plurality of discrete spatial sections within the sample, each discrete spatial section corresponding to one cycle step of the NMR experiment cycle.

Additionally, the spatial width, the phase, and the flip angle of each section can be independently varied by modulating the temporal extent, the phase, and the total power respectively of the associated component radiofrequency pulse prior to adding that component into the composite pulse. When applied, these pulses excite multiple sections simultaneously, allowing concurrent execution of multiple steps of a NMR experiment in multiple sections of the sample. Since otherwise these experiments would conventionally be executed sequentially, this speeds up total data acquisition time n-fold when n sections are used to perform n concurrent experiments.

Figure 2A:
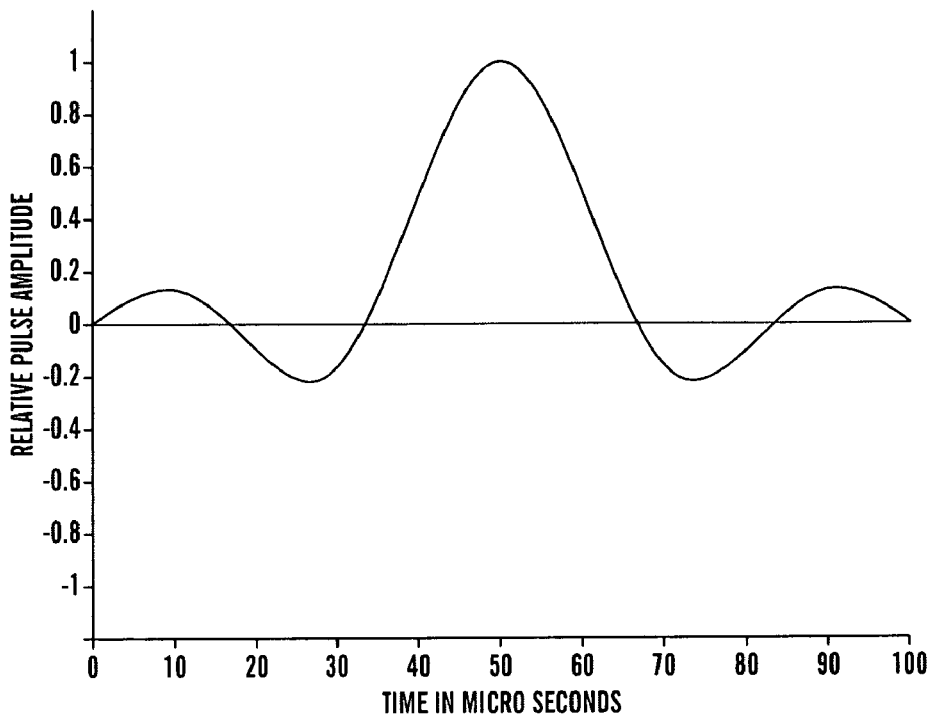
FIGS. 2A-C are graphs showing the temporal shape (FIG. 2A), Fourier transform (FIG. 2B), and empirical excitation profile (FIG. 2C) of a 3-lobed sinc pulse.

More specifically, the basic tool used for all types of simultaneous cycling is spatially selective excitation. Spatially selective excitation is performed by applying a shaped radiofrequency pulse concurrent with a z-axis pulsed field gradient (PFG) or "selection PFG" in order to deliver power from that radiofrequency pulse selectively to a limited fraction, for example a thin section, of the sample. A simple radiofrequency pulse sequence for performing spatially selective excitation is shown in FIG. 1. The shaped radiofrequency pulse used in FIG. 1 is a $\sin(\pi t)/(\pi t)$ or "sinc" shape as shown in FIG. 2A.

Figure 2B:
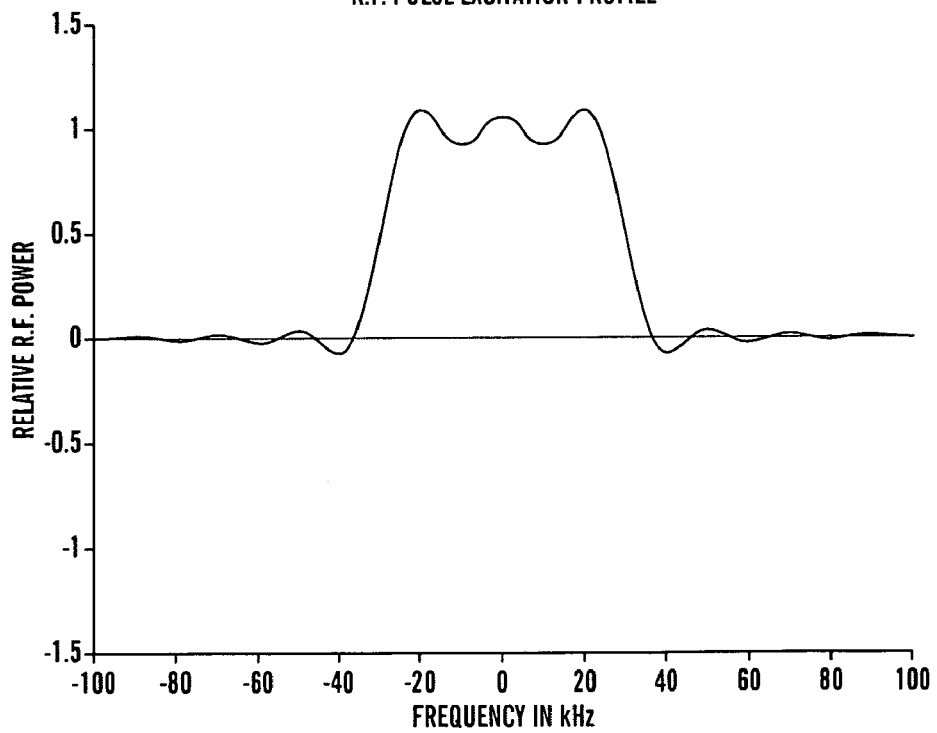
Figure 2C:
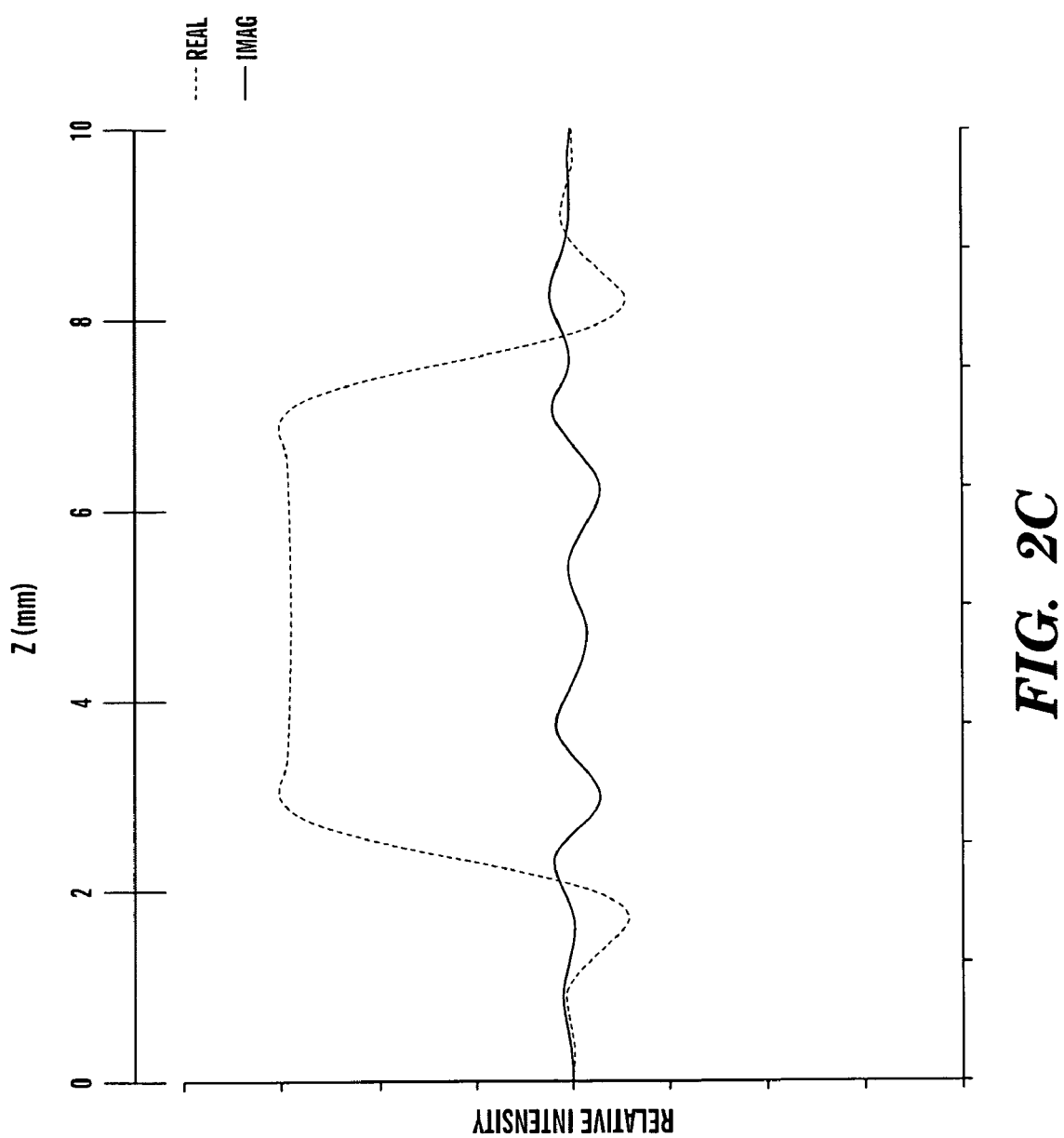

The concurrent PFG maps the spectral content of the shaped radiofrequency pulse into z-axis position in the sample. In approximation, the "spatial excitation profile" equals the Fourier transform of the temporal shape of the shaped radiofrequency pulse. The Fourier transform of a sinc shaped pulse is a rectangular or "rect" shaped spatial excitation profile as shown in FIG. 2B. The spatial excitation profile is not a perfect rectangle since the sinc shaped radiofrequency pulse has been truncated to only a center lobe and two side lobes on each side. An infinitely long sinc pulse is required to generate a perfectly rectangular profile after Fourier transformation. The experimentally acquired excitation profile for this pulse is shown in FIG. 2C. This profile shows additional non-idealities due to nonlinearities in the actual spatial excitation process compared with the Fourier transform. More complicated calculations and/or synthetic annealing can be used to design radiofrequency pulse shapes that produce more rectangular spatial excitation profiles for the same duration of radiofrequency pulse (Conolly et al., "Optimal Control Solutions to the Magnetic Resonance Selective Excitation Problem," *IEEE Transactions on Medical Imaging*, MI-5:016-115 (1986); Pauly et al., "Parameter Relations for the Sinnar-Le Roux Selective Excitation Pulse Design Algorithm," *IEEE Transactions on Medical Imaging*, 10:53-65 (1991); Kessler et al., "Multidimensional NMR Experiments Using Selective Pulses," *Magn. Reson. Chem.*, 29:527-557 (1991), which are hereby incorporated by reference in their entirety). Shaped radiofrequency pulses can be characterized in terms of a time-bandwidth product (TBP) (Schulte et al., "Design of Broadband RF Pulses with Polynomial-phase Response," *J. Magn. Reson.*, 186:167-175 (2007), which is hereby incorporated by reference in its entirety), which depends only on the shape of the pulse and can be determined either empirically or using Fourier transform theory. The TBP is defined in terms of the full width at half max (FWHM) of the pulse in both the time domain and the frequency domain as shown in Equation 1:

TBP=time domain *FWHM*(secs)*frequency domain *FWHM* (Hz)     (Equation 1)

For example, a three-lobed sinc pulse defined by $S(t)=\sin(\pi t)/(\pi t)$ for $-3<t<3$ has a TBP of six. The FWHM bandwidth for this pulse is then:

*FWHM* bandwidth(Hz)=6/pulse duration(s)     (Equation 2)

PFG amplitude is usually specified in Gauss/cm. However, for any particular nucleus, this can be readily converted to Hz/cm by multiplying by the gyromagnetic ratio, $\gamma$ (expressed in Hz/Gauss). The spatial extent or "section thickness" for a spatial excitation pulse is:

section thickness(cm)=bandwidth(Hz)/*PFG* strength (Hz/cm)     (Equation 3)

As an example, if one desired to excite the protons in a section of sample that is 0.25 cm thick using a three-lobed sinc pulse that is 100 µs in duration, the associated PFG amplitude would be

*PFG*=bandwidth/thickness or *TBP*/duration/thickness (Equation 4) or $$PFG(\text{Hz/cm}) = \frac{6}{100*10^{-6}s*0.25\,\text{cm}} = 240{,}000\,\text{Hz/cm or}$$

$$PFG(\text{Gauss/cm}) = \frac{PFG(\text{Hz/cm})}{\gamma(\text{Hz/Gauss})} = \frac{240{,}000\,\text{Hz/cm}}{4257\,\text{Hz/Gauss}} = 56.38\,\text{Gauss/cm}$$

The spatially selected region or "section" can be spatially offset from the center of the sample either by modulating the temporal shape of the radiofrequency pulse with a sinusoid of the appropriate frequency or by offsetting the transmitter frequency which will have the same effect. The offset frequency can be calculated based on the selection PFG amplitude and desired offset as shown in Equation 5:

Frequency(Hz)=*PFG* amplitude(Hz/cm)*Spatial Offset(cm)     (Equation 5)

For example, to move the section used in the calculation above by 0.5 cm the following offset frequency would be used:

Frequency(Hz)=240,000 Hz/cm*0.5 cm=120,000 Hz     (Equation 6)

To perform spatially selective excitation, a "selection PFG" is applied concurrent with a shaped radiofrequency pulse (FIG. 1). The PFG shifts the resonance frequency of all of the spins in the sample proportional to their position within the PFG (and thus within the sample) as shown in Equation 7:

$\omega(z)=\omega(0)+PFG*z$     (Equation 7), where z is spatial position along the z-axis defined by the main magnetic field, $B_0$, PFG is the PFG amplitude, and $\omega$ is the Larmor frequency. Therefore, the radiofrequency pulse is "off-resonance" or not quite at the Larmor frequency for all spins except those in the exact spatial center (z=0) of the PFG (and thus sample), where the value of the PFG is zero. An off-resonance radiofrequency pulse leads to a phase error, or "dephasing", $\beta$, which is a function of the frequency offset, $\Omega$, as shown in Equation 8 (Cavanagh et al., "Protein NMR Spectroscopy," Academic Press, San Diego (2007), which is hereby incorporated by reference in its entirety).

$$\tan(\beta) = (1-\cos\alpha)\sin\theta\frac{\Omega}{\omega_1\sin\alpha},$$     (Equation 8)

where $\omega_1=-\gamma B_1$ is the Larmor frequency experienced by the spins as a result of the radiofrequency field, $B_1$, and tan $\theta=\omega_1/\Omega$. For a rectangular excitation pulse ($\alpha=\pi/2$), and small frequency offsets ($\Omega<\omega_1$), Equation 8 yields:

$\beta\sim\Omega/\omega_1=\Omega*(\text{pulse width})*2/\pi$     (Equation 9).

Since this dephasing is first order proportional to the frequency offset, $\Omega$, the effect of the off-resonance radiofrequency pulse can be approximated by assuming an on-resonance pulse followed by an evolution period, tau=pulse width*2/π, during which the phase of the spins evolves due to the frequency offset imposed by the PFG (Cavanagh et al., "Protein NMR Spectroscopy," Academic Press, San Diego (2007), which is hereby incorporated by reference in its entirety).

However, a "sinc" shaped pulse with multiple lobes contains most of its energy in the middle of the pulse. For the purposes of estimating the dephasing of an off-resonance sinc pulse, a three lobed sinc pulse can be modeled as a rectangular pulse of duration pulse width*0.2 (the FWHM of a three lobed sinc pulse), followed by the remaining duration of the pulse (pulse width*0.4) during which we model the radiofrequency energy as 0 but the spins still evolve under the influence of the PFG. The dephasing for this pulse can then be approximated as $\beta\sim\Omega((\text{pulse width}*0.2)*2/\pi+(\text{pulse width}*0.4))$     (Equation 10), or $\beta\sim\Omega(\text{pulse width}*0.53)$.

Thus, an off-resonance, three-lobed sinc pulse can be modeled as an instantaneous, on-resonance pulse followed by an evolution period of duration tau≈pulse width*0.53.

The frequency offset and therefore the dephasing of each spin is proportional to its position in the selection PFG direction. The result is a linear dephasing in the direction of the selection PFG which can be removed by applying a "selection rephasing" PFG with the opposite polarity of the "selection PFG" for the same period tau. This "selection rephasing PFG" must be performed during a part of the pulse sequence where the desired coherences are transverse, since longitudinal spins are unaffected by application of a PFG. FIG. 1 shows the pulse sequence diagram for a simple spatially selective sinc pulse with associated selection PFG 1 and selection rephasing PFG 2. The exact strength of the rephasing PFG 2 was experimentally adjusted or "calibrated" to minimize dephasing by stepping PFG 2 through a range of values and selecting the value that maximizes the size of the desired signal.

In the present invention, no oscillating gradient (readout pulsed magnetic field gradient) or special processing is required for acquisition of the desired signal since the signals from each of the spatially discrete sections will add together automatically and the receiver will acquire the desired summation signal. Specifically, the radiofrequency pulse sequence can be re-arranged so that the receiver phase is constant for all steps of the cycle and the desired signal is the sum of the signals from each of the sections of the sample. In accordance with the present invention, the step of designing the cycle so that the receiver phase for each step of the cycle of the NMR experiment is the same will be dependent upon the cycle of the NMR experiment being conducted. Examples of designing of cycles so that the receiver phase for each step of the cycle of the NMR experiment is the same are shown in the Examples section below. Many cycling schemes can be effectively devised so that the receiver phase is constant for all steps of the cycle. In this case, no "readout" PFG is required during acquisition to separate the signals from the individual sections and the desired summation signal (i.e., joint detection of the signals from all sections) is picked up directly by the receiver.

One embodiment of the present invention relates to simultaneous radiofrequency pulse flip angle cycling NMR (SFC NMR). In this embodiment, each section of the sample is selectively affected by a portion of a composite radiofrequency pulse with an independent combination of flip angle and phase. The sections are of discrete size and their thickness reflects the weighting of the signal obtained with a given flip angle. In particular, the "weighting factor" defines the thickness of the section (or sections) associated with that flip angle. The composite radiofrequency pulses simultaneously excite all sections with associated flip angles, phases, and thicknesses as desired. Unlike the conventional variable flip angle experiments, in the present invention, all radiofrequency pulses need to be spatially selective in order to simultaneously apply different flip angles/phases and to ensure that the required receiver phase is zero for all sections.

Another embodiment of the present invention relates to simultaneous radiofrequency pulse phase cycling NMR (SPC NMR). In this embodiment, each section of the sample is selectively affected by a portion of a composite radiofrequency pulse with an independent phase. The sections are of discrete size and their thickness reflects the weighting of the signal obtained with a given set of phases. Unlike conventional phase cycled experiments, in the present invention, all radiofrequency pulses are spatially selective in order to simultaneously apply different phases to the sections while also ensuring that the required receiver phase is zero for all sections.

In principle, simultaneous phase cycling can be applied to any pulse sequence that requires phase cycling. The method can be extended to more complex phase cycling schemes by designing RF pulses with more sections, and using multiple "selective" RF pulses in a pulse sequence. In general, the minimal measurement time is reduced by a factor equal to the number of steps that are simultaneously executed, albeit at the expense of the signal to noise ratio (SNR). SNR is reduced by the ratio of the "section thickness" to the total sample length and further reduced due to the higher sampling bandwidths required for spatially resolved acquisition. However, in cases where equipment sensitivity and sample concentration are such that there is a surplus of SNR, simultaneous phase cycling is an attractive method for reducing acquisition time.

A further embodiment of the present invention relates to simultaneous pulsed magnetic field gradient strength cycling NMR (SGC NMR). In this embodiment, each section of the sample selectively experiences an independent effective pulsed magnetic field gradient strength. Simultaneously cycled pulsed magnetic field gradient cycling NMR relies on the fact that a $\pi$ pulse reverses the effect of a pulsed field gradient on transverse coherences. Thus, a spatially selective $\pi$ pulse in the middle of a train of one or more pulsed field gradient pulses will produce a net gradient pulse in the region that receives the $\pi$ pulse equal to the total pulsed field gradient strength prior to the $\pi$ pulse minus the total pulsed field gradient strength following the $\pi$ pulse. In contrast, coherences in the part of the sample that does not receive the spatially selective $\pi$ pulse receive a net gradient pulse equal to the sum of the strengths of all of the pulses in the pulse train. As a result, two or more steps of a pulsed field gradient strength cycle can be acquired simultaneously.

In accordance with the present invention, delays associated with pulsed field gradient pulses cause first order phase shifts in the resulting spectrum which are readily corrected during data processing. In another embodiment, additional "spin echo" sequences are added to the SFC/SPC/SGC pulse sequence to effectively remove the unwanted delays and associated phase shifts, as is well known in the art of NMR pulse sequence design (Cavanagh et al., "Protein NMR Spectroscopy," Academic Press, San Diego (2007), which is hereby incorporated by reference in its entirety).

Another aspect of the present invention relates to using the simultaneously cycled NMR method of the present invention to achieve coherence selection in a multidimensional NMR experiment in a single transient. In one embodiment, coherence selection is used for obtaining multiple-quantum filtered correlation spectrum. For example, double quantum filtered correlated spectroscopy (DQF COSY) experiments add a third radiofrequency pulse to a COSY experiment, where four step phase cycling is used to eliminate diagonal signals from uncoupled spins and to produce coupled spin diagonal and cross peaks that are in-phase. Accordingly, the method of the present invention can be useful for achieving coherence selection for such multiple-quantum filtered correlation spectrum in a single transient. In another embodiment, coherence selection is used for obtaining multiple-quantum correlation spectrum, where the multiple quantum coherence evolving in the indirect dimension is selected by the simultaneous phase cycle. In yet another embodiment, coherence selection is used for obtaining heteronuclear correlation spectrum.

Another aspect of the present invention relates to using the simultaneously cycled NMR method of the present invention to obtain a sub-spectrum of a G-matrix Fourier transformation (GFT) NMR experiment (Kim et al., *J. Am. Chem. Soc.*, 125:1385-1393 (2003); U.S. Pat. Nos. 6,831,459 and 7,365,539 to Szyperski et al.) from a single transient. GFT NMR spectroscopy reduces experiment time by encoding the information of higher-dimensional spectrum in fewer dimensions by co-incrementing indirect chemical shift evolution periods, and by independently cosine and sine modulating the detected signal in different data sets with the jointly sampled chemical shifts. After G-matrix transformation of these data sets, sub-spectra are obtained in which linear combinations of the jointly sampled chemical shifts are observed. A particular linear combination of data sets yielding a specific linear combination of chemical shifts can be simultaneously acquired using the simultaneously cycled NMR method. Thus, the method of the present invention can be useful for obtaining such sub-spectra from a single transient.

Yet another aspect of the present invention relates to using the method of the present invention to suppress spectral artifacts. The spectral artifacts can arise from incomplete suppression of NMR signals of a solvent in the sample. Alternatively, the spectral artifacts can arise from NMR polarization giving rise to axial peaks.

In a preferred embodiment, the NMR experiment is 2D [$^1$H,$^1$H]-E.COSY. E.COSY optimized for three-spin systems allows one to accurately measure vicinal $^1$H-$^1$H scalar ('J-') couplings and thus plays an important role in organic and natural product chemistry. In addition, E.COSY can be implemented (i) by cycling of radiofrequency pulse flip-angles, (Griesinger et al., *J. Chem. Phys.*, 85:6837-6852 (1986), which is hereby incorporated by reference in its entirety) (ii) by cycling of radiofrequency pulse phases, (Griesinger et al., *J. Chem. Phys.*, 85:6837-6852 (1986), which is hereby incorporated by reference in its entirety) or (iii) by co-addition of PFG coherence selected double-quantum filtered (DQF) and triple-quantum filtered (TQF) COSY spectra. (Willker et al., *J. Magn. Reson. Ser. A*, 102:348-350 (1992), which is hereby incorporated by reference in its entirety). Since (iii) requires that the strength of a PFG is varied when accomplishing DQ filtration versus TQ filtration, this approach is referred to as PFG strength cycling. Hence, E.COSY allows one to implement and compare three types of cycling schemes, that is, radiofrequency pulse flip-angle, radiofrequency pulse phase, and PFG strength cycling. The SC E.COSY congeners named, respectively, simultaneously flip-angle cycled (SFC), simultaneously phase cycled (SPC), and simultaneously gradient strength cycled (SGC) E.COSY, were implemented and compared, as set forth in the examples below. Simultaneous cycling in accordance with the present invention paves the way to design a large variety of SC NMR experiments with broad potential impact in natural science and engineering.

The radiofrequency pulsing and data acquisition for any one step of an NMR experiment takes up to many hundreds of milliseconds. To ensure longitudinal spin relaxation between the execution of the steps of an NMR experiment, a 'relaxation delay' has usually been introduced between the steps. During the relaxation delay, no data can be acquired so that his delay represents 'wasted time.' The total of the radiofrequency pulsing period, the data acquisition period, and the relaxation delay is known as the "repetition interval" of the experiment.

Spatially selective radiofrequency pulses can be used to confine an experiment step to a fraction of the total sample. Additional spatially confined experimental steps can then be conducted on other parts of the sample during the spin relaxation delay of this first experiment step. This technique is referred to herein as "section selective" NMR. Since both the radiofrequency pulsing and the data acquisition are done in a 'time multiplexed' manner, the data from each spatially separated step of the experiment is available for independent processing.

This idea of spatially separated, time multiplexed experiments (section selective NMR) is well known in the art of magnetic resonance imaging (MRI). Multiple (10-30) thin section, each in a different location, are imaged in a time multiplexed manner within each repetition interval.

In accordance with the present invention, the spatially selective radiofrequency pulses used for SC NMR can be designed to confine the SC NMR experiment to a fraction of the total sample. Additional SC NMR experiments can then be conducted in other parts of the sample during the relaxation delay of the first experiment, resulting in an experimental design that employs both the simultaneous cycling NMR method of the present invention and section selective NMR.

In one embodiment, the top and bottom halves of the sample are used to provide indirect dimension quadrature detection in a time multiplexed manner using section selective NMR while each half of the sample is further spatially partitioned using simultaneously cycled NMR. The data from the section selected top and bottom half are obtained in a time multiplexed manner and are thus available for the independent processing required for indirect dimension quadrature detection. All phase cycle steps plus indirect dimension quadrature detection for the NMR experiment are then condensed into a single repetition interval. In another embodiment, multiple fractions of the sample are used to obtain multiple sub-spectra of a G-matrix Fourier transformation (GFT) NMR experiment.

The following examples are provided to illustrate embodiments of the present invention but are by no means intended to limit its scope.

EXAMPLES

Example 1

Simultaneously Cycled (SC) 2D [$^1$H,$^1$H]-E.COSY

Figure 3A:
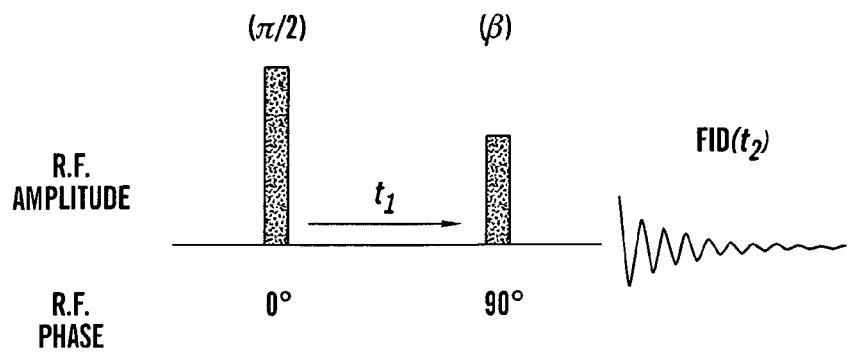
FIGS. 3A-C illustrate radiofrequency pulse schemes for conventional E.COSY (Griesinger et al., *J. Chem. Phys.*, 85:6837-6852 (1986); Griesinger et al., *J. Magn. Reson.*, 75:474-492 (1987); Willker et al., *J. Magn. Reson. Ser. A*, 102:348-350 (1992), which are hereby incorporated by reference in their entirety). Rectangular high power $^1$H pulses are indicated by vertical bars. The flip angles (in radians) and phases (in degrees) are indicated respectively above and below the bars and are provided in Table 1, below. The indirect and direct chemical shift evolution periods are denoted $t_1$ and $t_2$, respectively.
Figure 3B:
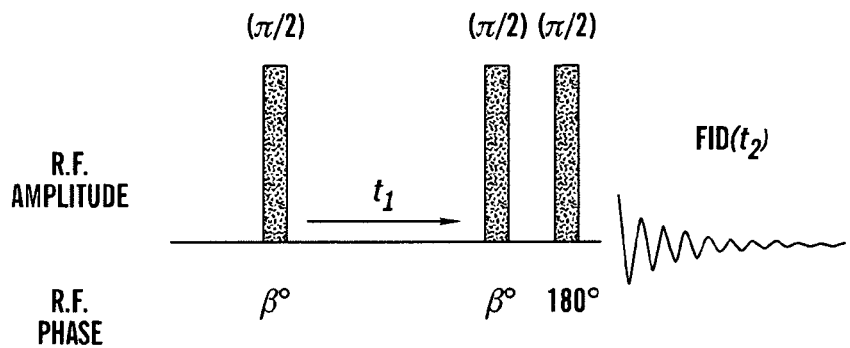
Figure 3C:
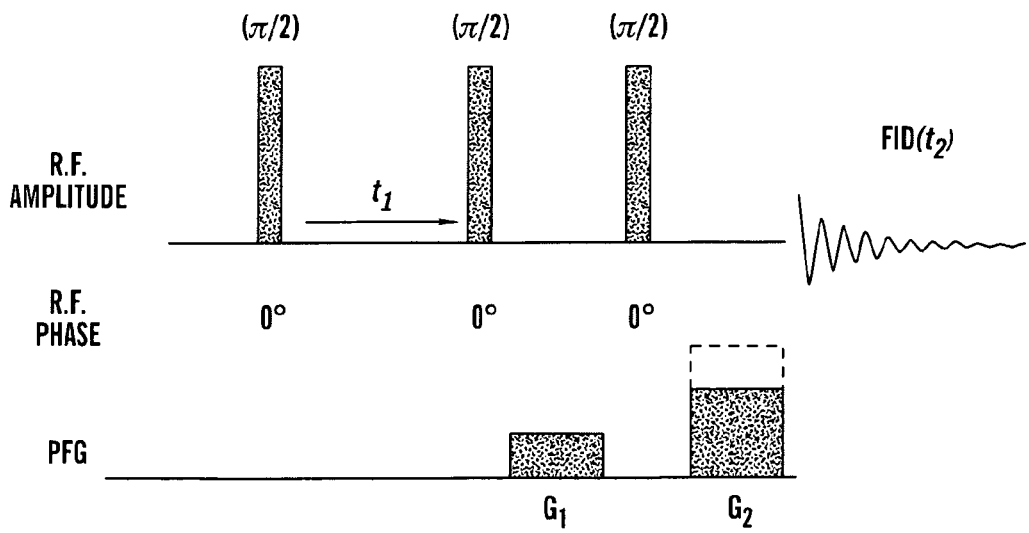

The radiofrequency pulse sequence of 2D [$^1$H,$^1$H]-COSY (Ernst et al., *Principles of Nuclear Magnetic Resonance in One and Two Dimensions*, Oxford Univ. Press: Oxford (1987), which is hereby incorporated by reference in its entirety) includes two $\pi/2$ flip-angle pulses separated by the indirect evolution period $t_1$. To avoid dispersive diagonal peaks which may occlude nearby cross-peaks, this pulse sequence is routinely expanded by a third $\pi/2$ radiofrequency pulse right before the start of signal detection. This enables implementation of DQF or TQF COSY (Ernst et al., *Principles of Nuclear Magnetic Resonance in One and Two Dimensions*, Oxford Univ. Press: Oxford (1987), which is hereby incorporated by reference in its entirety). E.COSY aims at simplifying the COSY cross-peak fine structure by selecting only cross peak components representing 'connected transitions' (Ernst et al., *Principles of Nuclear Magnetic Resonance in One and Two Dimensions*, Oxford Univ. Press: Oxford (1987), which is hereby incorporated by reference in its entirety). In turn, this allows one to accurately measure J-couplings (Griesinger et al., *J. Chem. Phys.*, 85:6837-6852 (1986); Griesinger et al., *J. Magn. Reson.*, 75:474-492 (1987); Willker et al., *J. Magn. Reson. Ser. A*, 102:348-350 (1992); Schroder et al., *Tetrahedron*, 54:12243-12248 (1998), which are hereby incorporated by reference in their entirety). Conventional E.COSY can be implemented in three different ways, and the corresponding radiofrequency pulse sequences are shown in FIGS. 3A-C. In order to properly distinguish radiofrequency pulse flip angles and phases, their values are given, respectively, in radians and degrees.

The flip-angle cycled E.COSY (FIG. 3A) uses the two radiofrequency pulse sequences of COSY to acquire multiple transients with a variable flip-angle, $\beta$, for the second radiofrequency pulse. For E.COSY optimized for 3-spin systems, the $\beta$ angle cycle and associated receiver phases are shown in Table 1 (flip angles are given in radians).

TABLE 1

Flip angle or Phase Cycle[a] for Conventional E.COSY Optimized for a 3 Spin System

| | | | | | |
|---|---|---|---|---|---|
| Flip Angle $\beta$ | 0 | $\pi/3$ | $2\pi/3$ | $4\pi/3$ | $5\pi/3$ |
| Pulse Phase $\beta°$ | 0° | 60° | 120° | 240° | 300° |
| Receiver Phase | 0° | 180° | 0° | 0° | 180° |
| Weight Factor (number of transients) | 4 | 3 | 1 | 1 | 3 |

[a]Flip angles and phases are, respectively, given in radians and degrees (FIG. 3A-C).

The weighting factor for each value of β is generally applied by repeating the experiment for that number of transients to ensure that each step of the cycle is weighted with corresponding S/N. Thus, such flip-angle cycled E.COSY requires 12 transients for each increment of the indirect evolution time $t_1$.

The phase cycled E.COSY (FIG. 3B) uses the three π/2 flip-angle pulse sequence of DQF/TQF COSY and multiple transients are acquired with varying radiofrequency pulse phases. The phase angles of the first two π/2 radiofrequency pulses, which are likewise denoted here as β take on the same values and number of transients as the flip-angles β in the flip-angle cycled E.COSY. In fact, flip-angle and phase angle cycled E.COSY are equivalent for ideal radiofrequency pulses (Griesinger et al., *J. Chem. Phys.*, 85:6837-6852 (1986), which is hereby incorporated by reference in its entirety). As in flip-angle cycled E.COSY, the weighting factor determines the number of FIDs recorded for a given value of β, thus likewise resulting in a minimum of 12 transients to implement the phase or flip-angle cycle for an E.COSY optimized for 3-spin systems (a minimum of 32 transients is required for E.COSY optimized for 4-spin systems). A further extended phase cycle is required if artifact suppression is desired in addition to the coherence selection.

E.COSY optimized for 3-spin systems represents a sum of DQF COSY and two times TQF COSY [if the DQF and TQF is accomplished by radiofrequency pulse phase cycling, the resulting phase cycle would then be longer than what is required for direct E.COSY acquisition (Table 1)]. Since single-transient DQF and TQF COSY can be implemented by using PFGs for coherence pathway selection (Hurd, *J. Magn. Reson. Ser. A*, 87:422-428 (1990), which is hereby incorporated by reference in its entirety), PFG coherence selected E.COSY represents the third way to implement E.COSY (Willker et al., *J. Magn. Reson. Ser. A*, 102:348-350 (1992), which is hereby incorporated by reference in its entirety) (FIG. 3C). This is accomplished by recording one transient with DQ filtration and two transients with TQ filtration, for which the re-phasing PFG2 (FIG. 3C) is adjusted, respectively, to twice or three times the strength of de-phasing PFG1. Since this corresponds to cycling the strength of PFG2, this E.COSY implementation is referred to as a gradient strength cycled E.COSY (FIG. 3C) which requires acquisition of three transients. Importantly, however, PFG-based coherence selection reduces the intrinsic sensitivity of DQF, TQF and thus E.COSY by a factor of two (Willker et al., *J. Magn. Reson. Ser. A*, 102:348-350 (1992), which is hereby incorporated by reference in its entirety). This makes the flip-angle cycled or radiofrequency pulse phase cycled implementation the preferred choice for many applications.

Simultaneously flip-angle, phase angle and gradient strength cycled E.COSY (FIGS. 4A-C) were implemented using the basic concepts to implement SC NMR devoid of readout PFGs, that is, (i) selective excitation of fractions of the NMR sample with each fraction being used to execute an individual step of the cycle, and (ii) design of a cycle having constant receiver phase (e.g., zero) for all steps. This ensures that the signal detected simultaneously from all sections represents the sum of FIDs required for E.COSY. For the present implementations, discrete "sections" within the NMR-active sample volume oriented orthogonally to the z-axis defined by the magnetic field $B_0$ were spatially selectively excited, and the relative thickness of the sections was chosen to reflect the weighting factors (Table 2).

TABLE 2

Pulse Phases and Flip Angles[a] for SFC E.COSY Optimized for a 3 Spin System

| | Section # | | | | | |
|---|---|---|---|---|---|---|
| | 1 | 2 | 3 | 4 | 5 | 6 |
| Pulse 1 Phase $\Phi_1$ | 0° | 0° | 180° | 180° | 0° | 0° |
| Pulse 2 Flip Angle β | 0 | 2π/3 | π/3 | π/3 | 2π/3 | 0 |
| Pulse 2 Phase $2\Phi_2$ | 90° | 90° | -90° | 90° | -90° | 90° |
| Receiver Phase[b] | 0° | 0° | 0° | 0° | 0° | 0° |
| Section Thickness | 2 | 1 | 3 | 3 | 1 | 2 |

[a]Flip angles and phases are, respectively, given in radians and degrees (FIG. 4A-C).
[b]Constant receiver phase is required to avoid readout gradients.

Notably, the finite duration of PFG pulses requires that first order phase corrections are applied during data processing. Compensating spin-echo modules could be incorporated to remove these corrections. However, this would lead to some loss of intrinsic sensitivity and was thus not pursued when designing the SC E.COSY schemes (FIGS. 4A-C) described in detail in the following examples.

Example 2

Simultaneously Flip-Angle Cycled (SFC) E.COSY

Figure 4A:
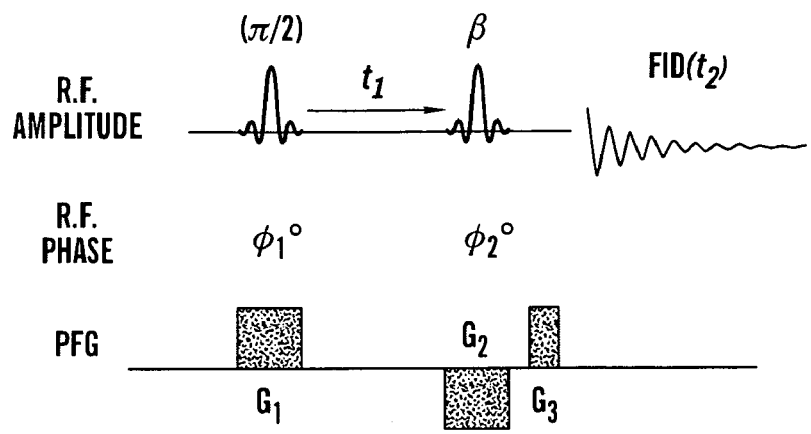
FIGS. 4A-C illustrate radiofrequency pulse schemes for simultaneously cycled (SC) E.COSY. Rectangular high-power $^1$H pulses are indicated by vertical bars. Selective $^1$H pulses are represented by a sinc-function indicating their shape and are applied concomitantly with PFGs indicated below the radiofrequency pulses and are thus spatially selective (for details, see FIG. 5). The flip angles (in radians) and phases (in degrees) are indicated, respectively, above and below the radiofrequency pulses. The values of β and Φ are provided in Tables 2 and 3, below.
Figure 5B:
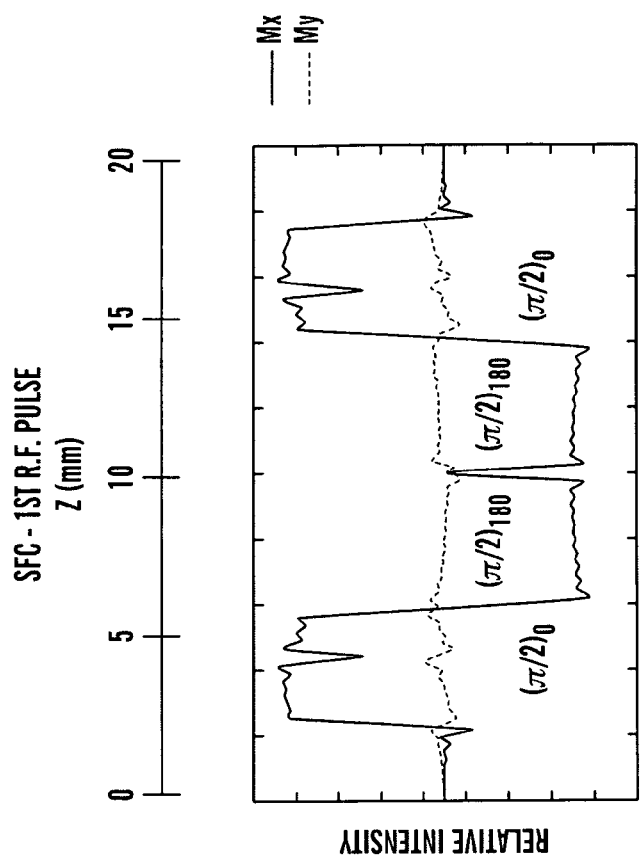
FIGS. 5A-J illustrate temporal radiofrequency pulse shapes and their experimentally determined spatial excitation profiles (see text) along the magnetic $B_0$-field defining the z-axis.
Figure 5A:
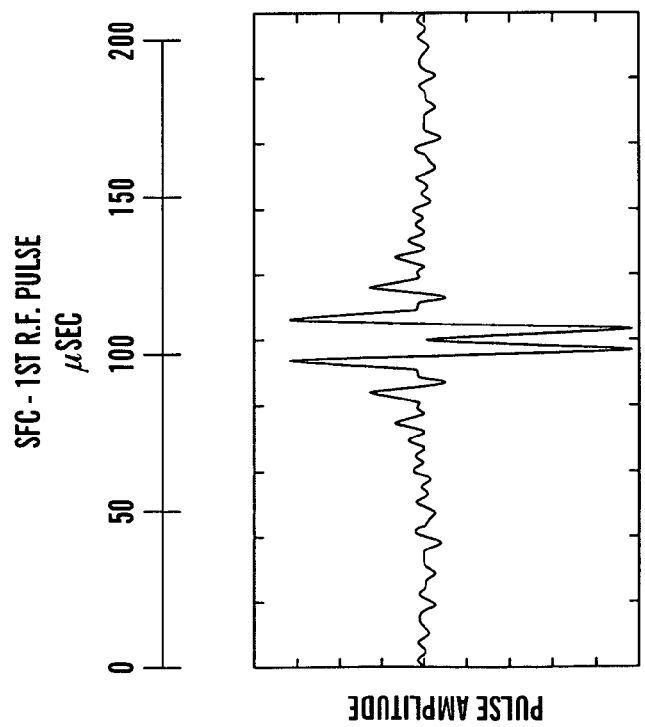
Figure 5D:
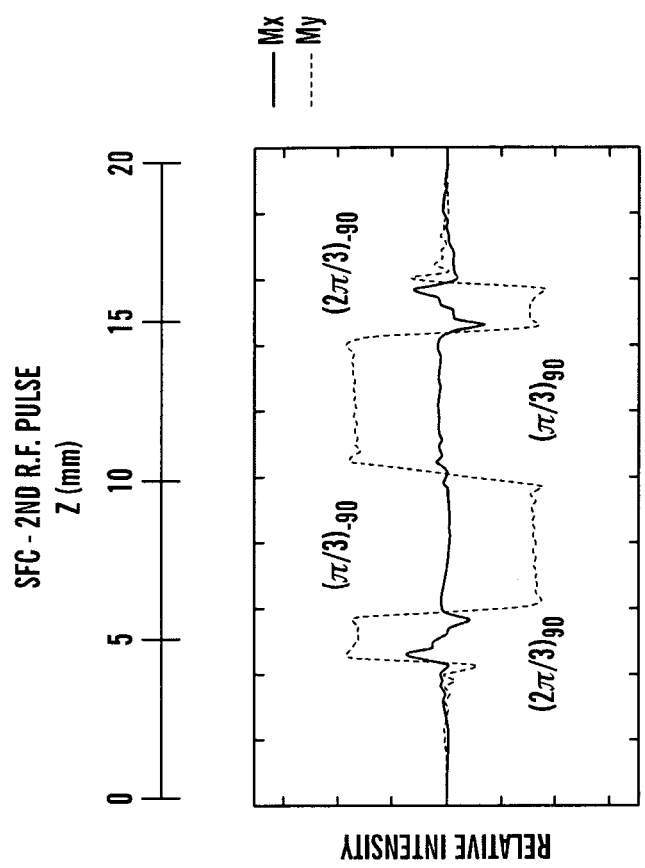
Figure 5C:
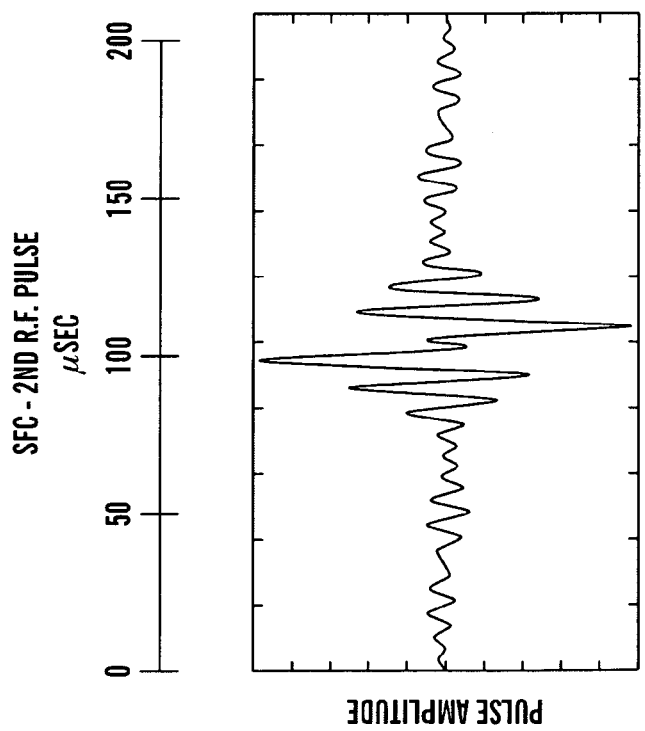
Figure 5F:
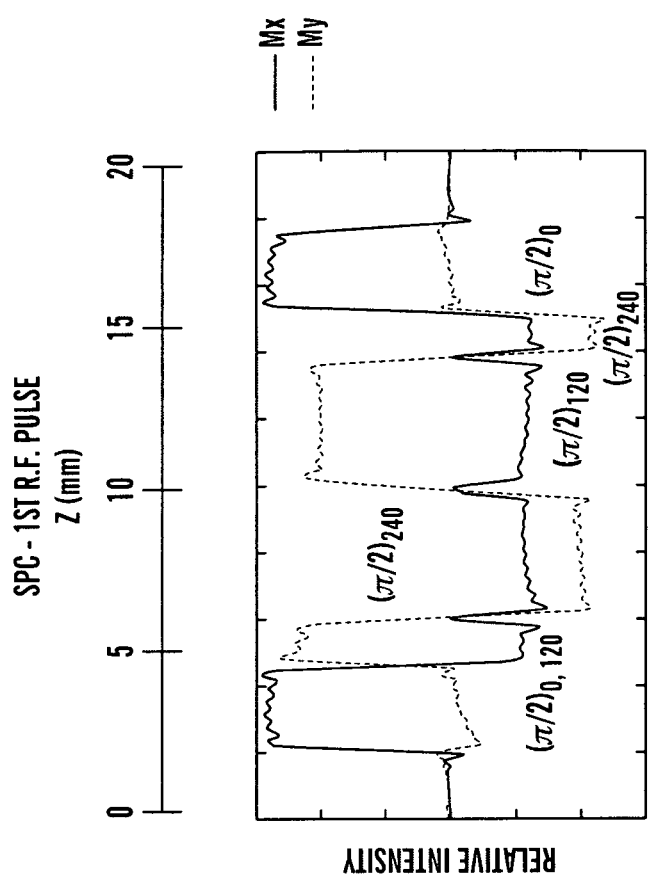
Figure 5E:
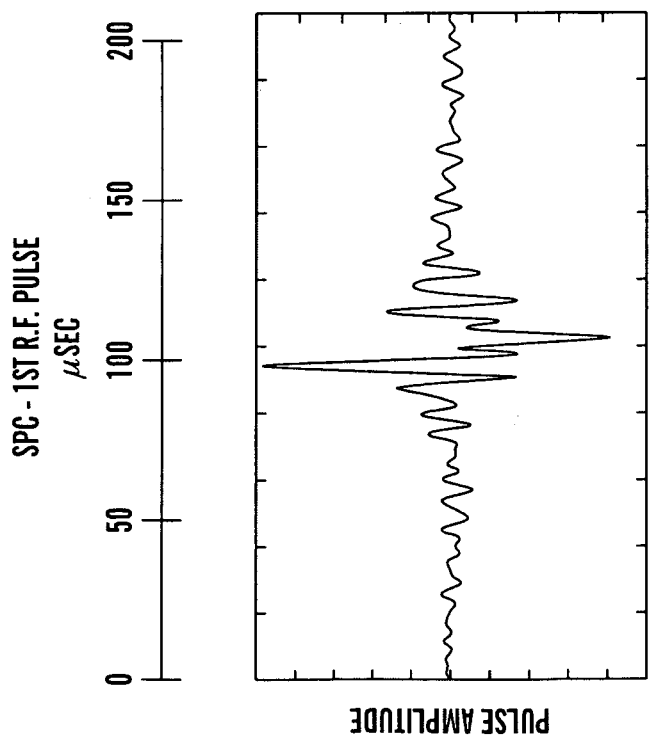
Figure 5H:
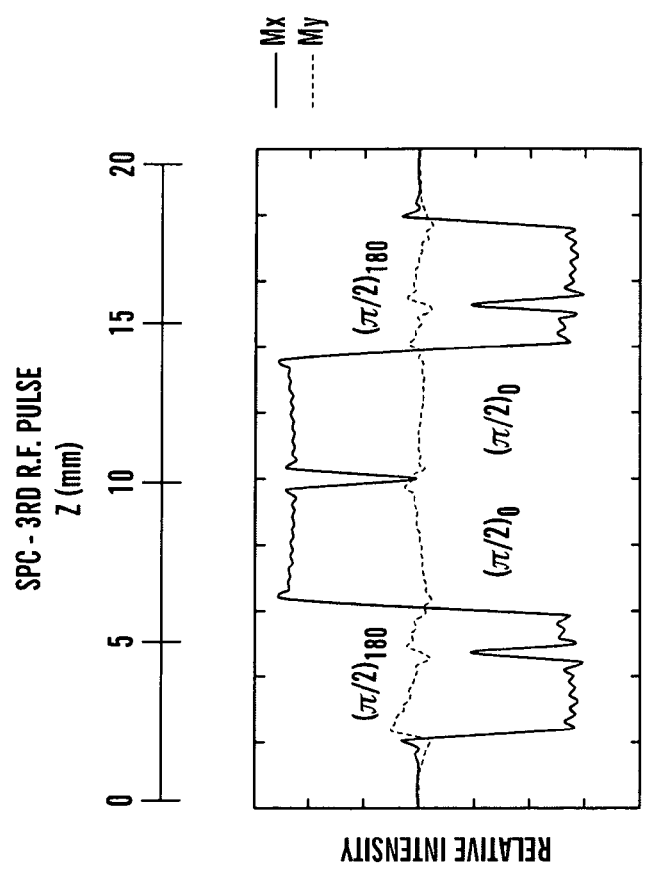
Figure 5G:
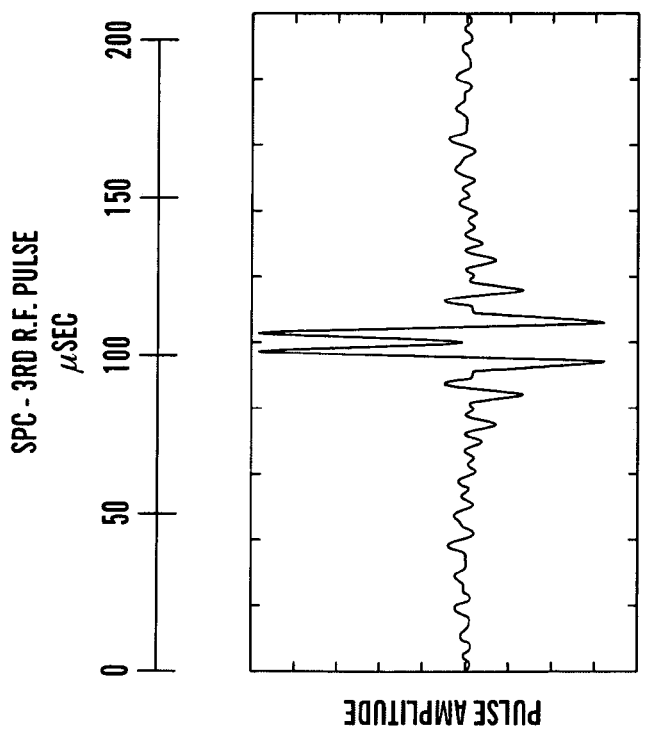

For SFC E.COSY (FIG. 4A), both radiofrequency pulses need to be spatially selective to ensure that the receiver phase can be set to zero for all steps of the cycle. Each of the two radiofrequency pulses affect six different sections with different radiofrequency pulse flip-angles, β, and phases, $\Phi_1$ and $\Phi_2$, to execute the required flip-angle cycle with a single transient. The values for β, $\Phi_1$, and $\Phi_2$ were derived from the conventional cycle (Table 1), i.e., for steps with β=π+α>π, the phase of the radiofrequency pulse was changed by 180° and the flip-angle was set to π-α, while for steps with a 180° receiver phase shift that phase shift was instead applied to both radiofrequency pulses (Table 2). Two composite radiofrequency pulses were then created as the sum of individual radiofrequency pulses affecting individual sections. These simultaneously excite the six sections with flip-angles, phases and section thicknesses as shown in Table 2. The temporal waveforms and experimentally determined spatial excitation profiles of the two selective pulses of SFC E.COSY (FIG. 4A) are shown, respectively, in FIGS. 5A and 5B (waveform and excitation profile of the first radiofrequency pulse) and FIGS. 5C and 5D (waveform and excitation profile of the second radiofrequency pulse). A technical comment relates to the fact that the PFG strengths need to be accurately adjusted to ensure that desired coherences are not partially de-phased. The strengths of PFG 1 and PFG 2 were adjusted to select the desired section thicknesses given the spectral width of the spatially selective radiofrequency pulse. PFG 2 was inverted so as to re-phase the de-phasing of desired coherences by PFG 1 and the excess de-phasing of PFG 2 was re-phased by PFG 3. (During about the first half of PEG 1, the magnetization is largely longitudinal and thus not affected by the PFG.)

Example 3

Simultaneously Phase Cycled (SPC) E.COSY

For SPC E.COSY (FIG. 4B), three spatially selective $\pi/2$-flip-angle radiofrequency pulses were applied affecting six different sections with different pulse phases $\Phi_1$, $\Phi_2$, and $\Phi_3$ (Table 3).

TABLE 3

Pulse Phases for SPC E.COSY Optimized for a 3 Spin System

| | Section # | | | | | |
|---|---|---|---|---|---|---|
| | 1 | 2 | 3 | 4 | 5 | 6 |
| Pulse 1 Phase $\Phi_1$ | 0° | 120° | 240° | 120° | 240° | 0° |
| Pulse 2 Phase $2\Phi_2$ | 0° | 240° | 120° | 240° | 120° | 0° |
| Pulse 2 Phase $2\Phi_3$ | 180° | 180° | 0° | 0° | 180° | 180° |
| Receiver Phase[a] | 0° | 0° | 0° | 0° | 0° | 0° |
| Section Thickness | 2 | 1 | 3 | 3 | 1 | 2 |

Figure 4B:
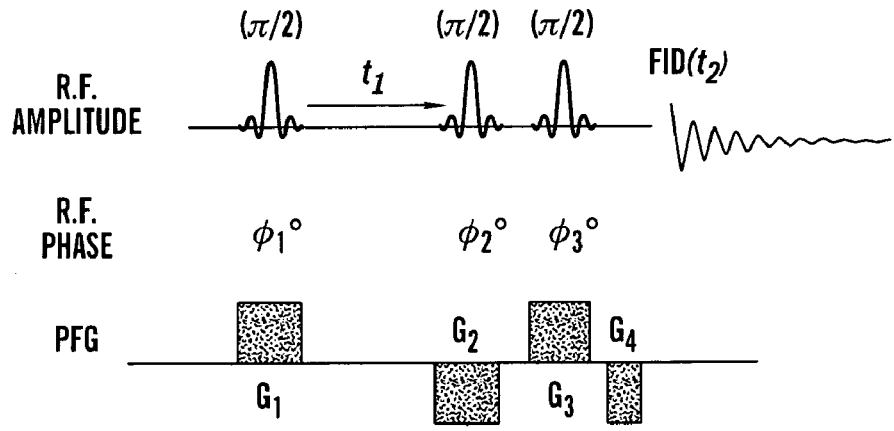

[a]Constant receiver phase is required to avoid readout gradients (FIG. 4B).

The values for $\Phi$ were derived from the conventional cycle (Table 1) by increasing the radiofrequency pulse phases for steps with a receiver phase of 180° by that amount. This ensures that the receiver phase can be set to zero for all sections (Table 3). Three composite radiofrequency pulses were then created as the sum of individual radiofrequency pulses affecting individual sections. The temporal waveforms and experimentally determined spatial excitation profiles of the first and third selective radiofrequency pulses of SPC E.COSY (FIG. 4B) are shown, respectively, in FIGS. 5E and 5F, and 5G and 5H. The second radiofrequency pulse is the same as the first one, except for reversal of the order of sections to compensate for the reversal of the gradient polarity for PFG 2. The PFG strengths in SPC E.COSY likewise need to be set accurately. The strengths of PFG 1, PFG 2, PFG 3, and PFG 4 were adjusted to select the desired section thicknesses given the spectral width of the spatially selective radiofrequency pulse and to ensure that overall de-phasing and re-phasing of the PFGs were equal.

Example 4

Simultaneously Gradient-strength Cycled (SGC) E.COSY

For SGC E.COSY, the conventional radiofrequency pulse sequence (FIG. 3C) was modified by introducing a spatially selective $\pi$-pulse right before signal detection (FIG. 4C) and relies on the fact that de-phasing of coherences by PFGs can be effectively re-phased by applying a $\pi$-pulse (Cavanagh et al., *Protein NMR Spectroscopy*, Academic Press: San Diego (2007), which is hereby incorporated by reference in its entirety). In general, a spatially selective $\pi$-pulse in the middle of a train of one or more PFG pulses will produce a net gradient pulse in the region that is affected by the $\pi$ pulse equal to the total PFG strength prior to the $\pi$ pulse minus the total PFG strength following the $\pi$ pulse. In contrast, coherences in sections not affected by the selective $\pi$ pulse receive a net gradient pulse equal to the sum of the strengths of all of the pulses in the pulse train. As a result, different sections experience different PFG strengths so that PFG strength cycling can be implemented. For E.COSY optimized for three-spin systems, the sum of a DQF and two times a TQF COSY needs to be acquired. Hence, a spatially selective $\pi$ radiofrequency pulse in the middle of PFG 2 followed by PFG 3 having twice the strength of PFG 1 is introduced. The section thickness of the spatially selective $\pi$ pulse was adjusted so that one third of the sample experienced no net gradient from PFG 2. Hence, only double quantum coherences were re-phased by PFG3 in this section, while the remaining two thirds of the sample was not affected by the $\pi$ pulse so that PFG2 and PFG3 serve to re-phase triple quantum coherences. The resulting signal yielded the desired SGC E.COSY spectrum. The temporal waveform and experimentally determined spatial excitation profile for the spatially selective $\pi$-pulse used for SGC E.COSY are shown, respectively, in FIGS. 5I and 5J, respectively.

Example 5

Composite Radiofrequency Pulses for SC E.COSY

Selective radiofrequency pulses must be chosen for implementing SC NMR (FIGS. 5A-J) in this approach. Composite shaped radiofrequency pulses were generated using the program Matlab® (The Math Works Inc.). The temporal radiofrequency pulse shapes corresponding to each section, with desired section thickness and offset from center, were individually generated and then added to create the composite radiofrequency pulse.

The temporal shape, $S_1(t)$, of the radiofrequency pulse exciting only the thinnest section 1 (defining a relative width of 1.0) was represented by the three central lobes of a sinc function, that is, $S(t)=\sin(t)/t$ for $-3\pi<t<3\pi$ digitized with 200 points and having a time-bandwidth product (TBP) (Schulte et al., *J. Magn. Reson.*, 186:167-175 (2007), which is hereby incorporated by reference in its entirety) of six. Hence, the radiofrequency pulse selectively exciting a section 2 with relative thickness 2.0 is given by $S_2(t)=\sin(t)/t$ for $-6\pi<t<6\pi$ digitized with 200 points. In order to shift the center of excitation of the second pulse by a relative distance of 1.65 so as to make it adjacent to section 1 with 110% spacing of the centers of excitation in order to mitigate section to section interference, $S_2(t)$ is time shifted according to $S_{2,offset}(t)=S_2(t)\exp(i*1.65*2*t)$ for $-3\pi<t<3\pi$ with 200 points. The shapes $S_{n,offset}(t)$ of radiofrequency pulses exciting additional sections were generated accordingly, and the summation of all individual shapes yields the shape for the composite radiofrequency pulse, $S_{comp}(t)$. Since the desired excitation profile for each of the individual radiofrequency pulses is hermitian (the profile is its own conjugate transpose), the temporal shapes possess no imaginary component. The composite radiofrequency pulses become spatially selective by applying them concurrently with a z-axis PFG, and the radiofrequency pulse bandwidth divided by the amplitude of the PFG yields the thickness $\Delta z$ of the excited section, where the pulse bandwidth is given by the time-bandwidth product divided by the pulse duration. (During selective excitation, the chemical shifts of different nuclei within the sample will result in a different spatial offset of the selected section for each nuclei. However, in the presence of PFGs with strengths employed for the present study (FIGS. 4A-C), this offset is negligibly small even for chemical shifts of tens of ppm.)

Excitation profiles (FIGS. 5A-J) were experimentally determined by applying the composite radiofrequency pulse with shape $S_{comp}(t)$ to a sample of about 1% $H_2O$ dissolved in $D_2O$. During acquisition, a z-axis "readout" PFG was applied (which encodes z-axis position as frequency) so that a FT of the acquired signal yields the spatial excitation profile. For the selective π pulse (FIGS. 5I and 5J), a rectangular π/2 pulse was applied before the π pulse which then selectively inverts the transverse magnetization.

Example 6

Applications of SC NMR

COSY spectra were recorded with two samples, that is, (i) a 100 mM solution of the proteinogenic amino acid tyrosine dissolved in $D_2O$ at pD=10, and (ii) a 30 mM solution of the plant solanum-steroid-alkaloid tomatidine (Willker et al., *Magn. Reson. Chem.*, 30:645-650 (1992); Raffauf, *Plant Alkaloids: A Guide to Their Discovery and Distribution*.; Haworth Press: (1996), which are hereby incorporated by reference in their entirety) [(3β,5α,25Σ)-spirosolan-3-ol; CAS number 77-59-8)] dissolved in pyridine. Data were acquired on a Varian INOVA 500 spectrometer equipped with a conventional $^1H\{^{13}C,^{15}N,^{19}F\}$ probe, processed using the program NMRPipe (Delaglio et al., *J. Biomol. NMR*, 6:277-293 (1995), which is hereby incorporated by reference in its entirety) and analyzed using the program NMRDraw. (Delaglio et al., *J. Biomol. NMR*, 6:277-293 (1995), which is hereby incorporated by reference in its entirety).

SC E.COSY experiments (FIGS. 4A-C) were implemented and compared in terms of intrinsic sensitivity and performance using a 100 mM solution of the proteinogenic amino acid tyrosine in $D_2O$. Tyrosine contains two diasterotopic $^2J$-coupled β-protons with non-degenerate chemical shifts which are themselves coupled by $^3J_{\alpha\beta}$-couplings solely to the α-proton. Hence, the $^1H^\alpha\text{-}^1H^{\beta 2}\text{-}^1H^{\beta 3}$ spin system of tyrosine allows one to accurately compare intrinsic sensitivity and quality of E.COSY peak pattern detection. The thus optimized implementations were applied to obtain E.COSY spectra for a 30 mM solution of the 416 Da plant alkaloid tomatidine dissolved in pyridine. Tomatidine exhibits $^1H$ chemical shifts dispersed over a range of about 4.2 ppm, and the resulting high-quality SC E.COSY NMR spectra demonstrate the versatility of SC NMR for routine applications in organic and natural product chemistry.

Figure 4C:
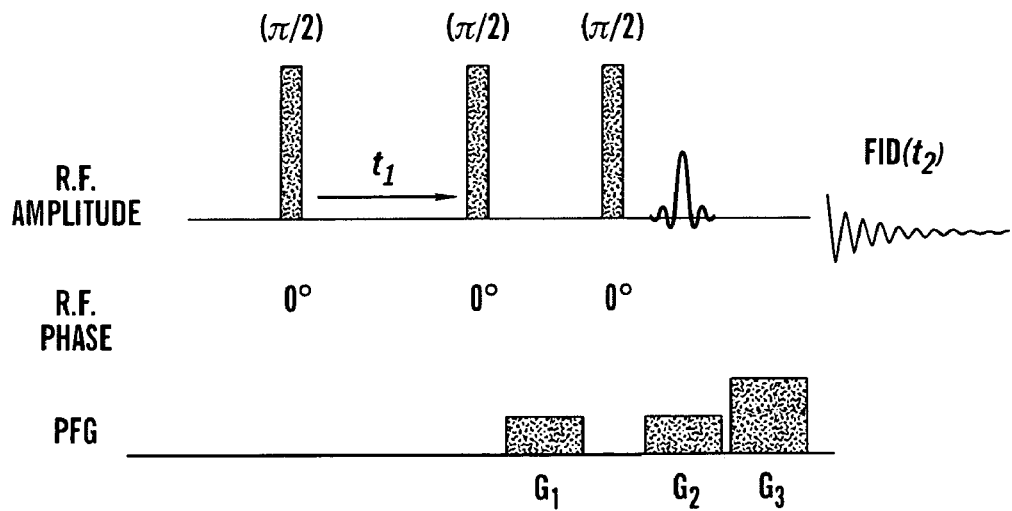
Figure 5J:
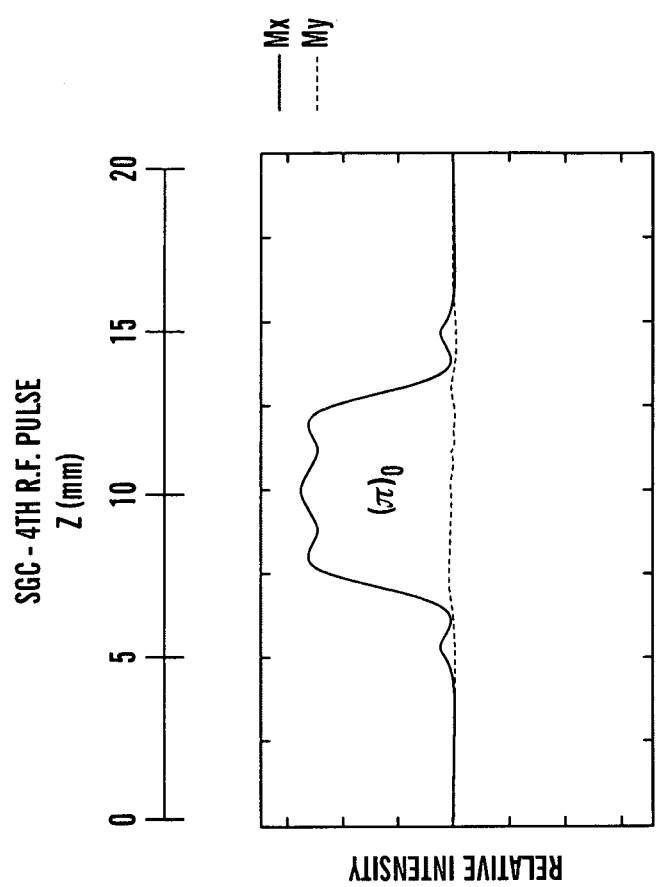
Figure 5I:
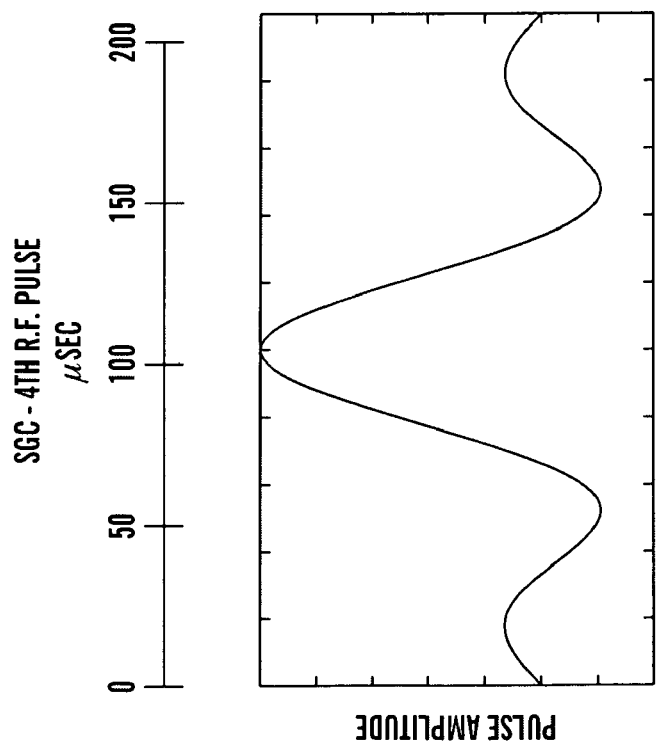
Figure 6A:
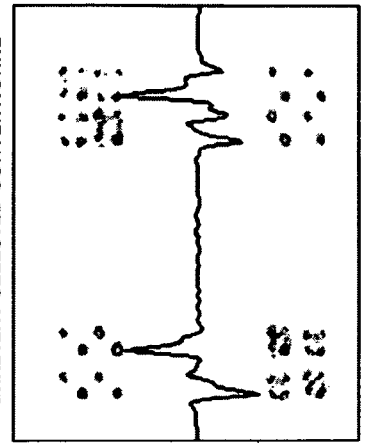
FIGS. 6A-F show spectral regions comprising peaks detected on $^1H^{\beta 2}$ and $^1H^{\beta 3}$ of tyrosine taken from a simulation (FIG. 6A) and E.COSY spectra (FIGS. 6B-F), as indicated above the panels, recorded with 256 complex points and 500 Hz spectral width in both dimensions ($t_{max}$=512 ms), and a relaxation delay, $\tau_{rel}$, between scans of two seconds yielding a total relaxation time of 2.51 seconds. The time-domain data were multiplied with cosine function and zero-filled two times before FT, which resulted in a digital resolution of 0.98 Hz/point.
Figure 6B:
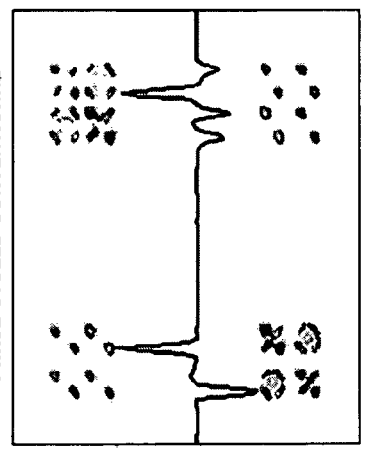
Figure 6C:
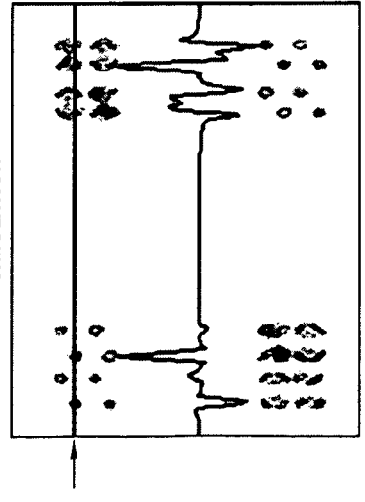
Figure 6D:
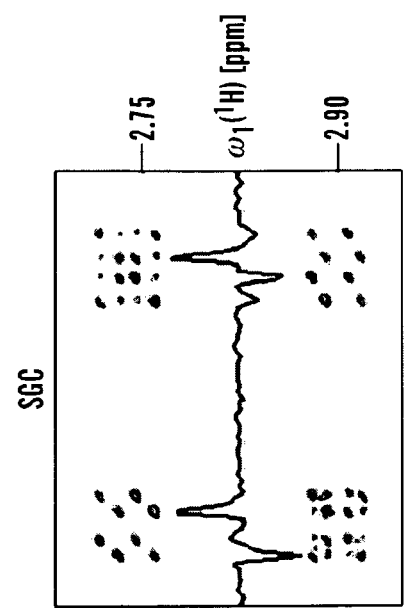
Figure 6E:
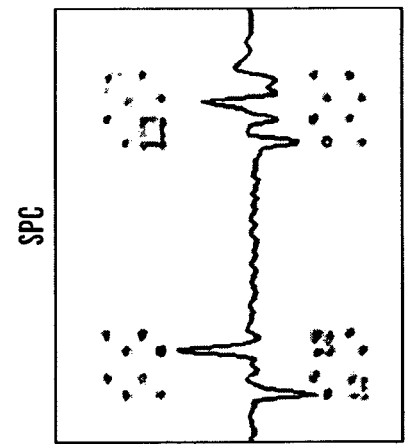
Figure 6F:
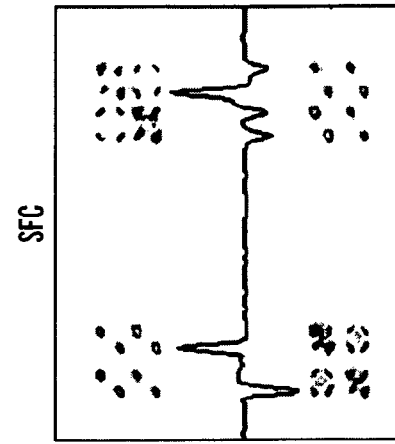

FIGS. 6A-F show spectral regions of E.COSY spectra comprising the cross peaks detected on $^1H^{\beta 2}$ and $^1H^{\beta 3}$ of tyrosine. As a reference, peaks were simulated with known chemical shifts and scalar couplings using the program QSIM (Helgstrand et al., *J. Biomol. NMR*, 30:71-80 (2004), which is hereby incorporated by reference in its entirety) (FIG. 6A). Regions taken from conventional radiofrequency pulse phase cycled (measurement time: 285 minutes) and PFG coherence selected E.COSY spectra (measurement time: 72 minutes) are shown in FIGS. 6B and 6C, respectively. Comparison with SFC (FIG. 6D), SPC (FIG. 6E) and SGC E.COSY (FIG. 6F) spectra recorded within 24 minutes shows that the NMR data acquisition allows accurate selection of the desired E.COSY cross peak fine structure with all three SC E.COSY schemes (FIGS. 4A-C).

Furthermore, the S/N ratios were measured for these cross peaks, and in order to compare intrinsic sensitivity these ratios were divided by the square root of the acquisition time (Table 4).

TABLE 4

Signal to Noise Ratio for Conventional and Simultaneous Cycled E.COSY

| Experiment | Number Transients | S/N | S/N/√t[a] |
|---|---|---|---|
| Conventional E.COSY | | | |
| phase cycled | 12 | 160 | 46 |
| PFG cycled | 3 | 23 | 16 |
| SC E.COSY | | | |
| flip-angle cycled | 1 | 30 | 30 |
| phase cycled | 1 | 17 | 17 |
| gradient selected | 1 | 13 | 13 |

[a]t defines the total measurement time

For conventional phase cycled and gradient selected E.COSY normalized S/N ratios of 46 and 16 were obtained, respectively. As expected (Willker et al., *J. Magn. Reson. Ser. A*, 102:348-350 (1992), which is hereby incorporated by reference in its entirety), the incorporation of the two additional PFGs for coherence selection reduced the intrinsic sensitivity somewhat below the theoretically predicted factor of two. For SC E.COSY, the normalized S/N ratios (Table 4) turned out to be 30 for SFC (65% of conventional phase cycled E.COSY), 17 for SPC (37% of conventional phase cycled E.COSY) and 13 for SGC E.COSY (76% of conventional PFG coherence selected E.COSY). For SFC and SPC E.COSY, the loss of intrinsic sensitivity relative to conventional E.COSY is primarily due to (i) imperfections of shaped radiofrequency pulses, (ii) imperfect re-phasing of desired coherences, and (iii) the fact that the spatially selected sections are separated by gaps which do not contribute to the detected signal (FIGS. 5A-J). However, since the intrinsic sensitivity of currently implemented SFC E.COSY (FIG. 4A) reaches 65% of what is registered for conventionally phase cycled E.COSY, it is evident that this SC NMR experiment is valuable for routine applications. The rather low intrinsic sensitivity of SPC E.COSY is due to the fact that three spatially selective radiofrequency pulses are required (FIG. 4B). It is likely that the sensitivity for each of the SC methods can be improved by refining of the composite radiofrequency pulses using convex optimization (Conolly et al., *Abstracts of the Society of Magnetic Resonance in Medicine*, 958 (1985); and Kessler et al., *Magn. Reson. Chem.*, 29:527-557 (1991), which are hereby incorporated by reference in their entirety) or direct waveform synthesis (Le Roux, *Abstracts of the Society of Magnetic Resonance in Medicine*, 1049 (1988), which is hereby incorporated by reference in its entirety).

The observed intrinsic sensitivities (Table 4) are in agreement with Bloch simulations which predict that each spatially selective radiofrequency pulse acting on either longitudinal magnetization or on transverse magnetization reduces the intrinsic sensitivity by about 20%. A single spin Bloch simulation was implemented using Matlab. The simulation assumed ideal radiofrequency pulses and PFG waveforms. Spatially selective radiofrequency pulses were applied and the desired component of the final magnetization was integrated over the spatially selective section and compared to a perfect transfer of magnetization. Hence, a prime goal when designing SC NMR experiments must be to reduce the number of selective radiofrequency pulses to a minimum. The relatively high sensitivity of SGC E.COSY (76% relative to the conventional PFG coherence selected E.COSY) is due to the fact that only about a third of the sample receives any selective pulse at all. While this portion of the sample does incur some loss (about 20%) due to the imperfect nature of the selective π radiofrequency pulse, the remaining ⅔ of the sample contribute the same amount of signal as in the conventional study. Note, however, that SGC E.COSY is per se a factor of two less sensitive than SFC and SPC congeners.

Overall, SFC E.COSY was the most sensitive of the SC E.COSY experiments presented here. A practical advantage of least sensitive SGC E.COSY is that it is most robust with respect to inaccurate PFG calibration because PFG DQ and TQ filtration per se efficiently suppresses undesired dispersive peak components.

Example 7

Application of SFA E.COSY: Spectrum Acquired for the Alkaloid Tomatidine

Figure 7A:
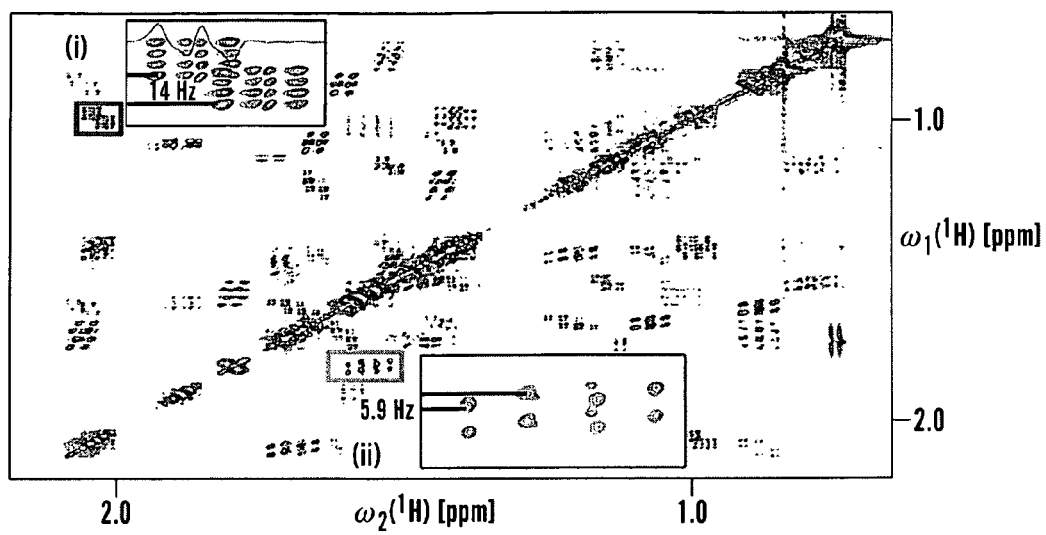
FIG. 7A illustrates a spectral region taken from SFC E.COSY recorded for plant alkaloid tomatidine (Willker et al., *Magn. Reson. Chem.*, 30:645-650 (1992), which is hereby incorporated by reference in its entirety) with 1,024 complex points along $t_1$, 1,536 complex points along $t_2$, and 2,500 Hz spectral width in both dimensions yielding $t_{1,max}$=410 ms and $t_{2,max}$=614 ms, and a delay, $\tau_{rel}$, between scans of 1.5 seconds, yielding a total $T_1$-relaxation delay of 2.1 seconds. The time-domain data were multiplied with a cosine function and zero-filled four times in both dimensions, yielding after FT a digital resolution of, respectively, 0.6 Hz/point and 0.4 Hz/point for $\omega_1$ and $\omega_2$. Expanded cross peaks used to measure J-couplings are shown in two insets.
Figure 7B:
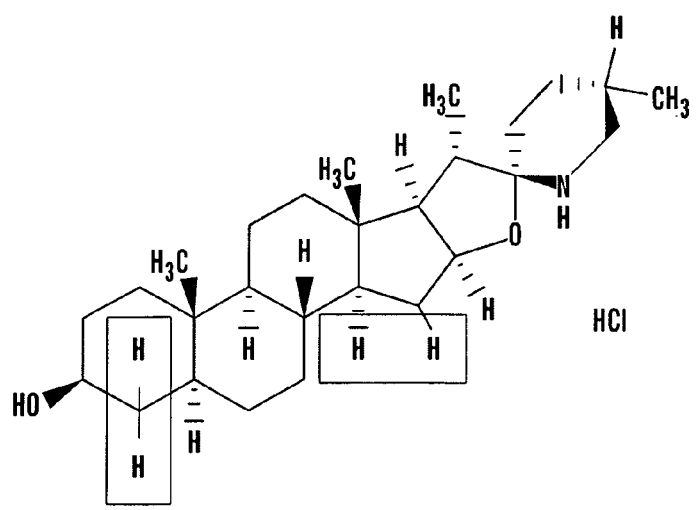
FIG. 7B is the chemical structure of tomatidine.

A highly resolved SFC E.COSY spectrum ($t_{1,max}$=410 ms, $t_{2,max}$=614 ms) was recorded in 80 minutes for tomatidine (FIG. 7A). For comparison, a conventional phase cycled E.COSY spectrum was recorded, which required 960 minutes of measurement time, that is, 12 times longer. Representative cross peaks exhibit S/N ratios of about 200 in this spectrum, demonstrating that conventional data acquisition is pursued in the sampling limited acquisition regime. In SFA E.COSY, cross peak detection is complete and the corresponding S/N ratios in the SFA E.COSY experiment are still about 50. Due to the high spectral resolution, this enables one to accurately measure $^3$J-couplings.

In contrast to SFA E.COSY, measurement of J-couplings in conventional phase cycled DQF COSY (320 minutes measurement time) is impeded by intricate cross peak fine structures: the cross-peak arising from the spin system which is detected on $^1H^{15\alpha}$ (2.03 ppm; FIG. 7A, inset i) enables accurate measurement of $^3J(14-15\beta)$=14.0 Hz in E.COSY only (a cross-section taken along $\Omega_2$ shows that the peak components corresponding to undesired transitions were almost completely eliminated). Similarly, the cross peak arising from the spin system comprising detected on $^1H^{4\beta}$ (1.55 ppm; FIG. 7A, inset ii) yields accurate measurement of $^3J(4\alpha-3)$=5.9 Hz.

Example 8

Design of a Suite of SC NMR Experiments

The principles of SC NMR set forth herein allow one to design a suite of SC NMR experiments for a large range of different applications except when independent acquisition of the signals of the cycle steps is required as in, for example, pure absorption mode quadrature detection (Ernst et al., *Principles of Nuclear Magnetic Resonance in One and Two Dimensions*, Oxford Univ. Press: Oxford (1987), Cavanagh et al., *Protein NMR Spectroscopy*, Academic Press: San Diego (2007), which are hereby incorporated by reference in their entirety).

First, considering the corresponding flip angle or phase cycles (Griesinger et al., *J. Chem. Phys.*, 85:6837-6852 (1986); Griesinger et al., *J. Magn. Reson.*, 75:474-492 (1987), which are hereby incorporated by reference in their entirety), it is straightforward to extend the SC E.COSY cycling (optimized here for 3-spin systems) to larger spin systems.

Second, all 2D [$^1$H,$^1$H] NMR experiments consisting of two or three radiofrequency pulses are amenable to SC NMR in a straightforward manner, as exemplified here for E.COSY. Those include all variations of 2D multiple-quantum and multiple-quantum filtered NMR experiments (Ernst et al., *Principles of Nuclear Magnetic Resonance in One and Two Dimensions*, Oxford Univ. Press, Oxford (1987), which is hereby incorporated by reference in its entirety) as well as 2D [$^1$H,$^1$H] NOESY (Ernst et al., *Principles of Nuclear Magnetic Resonance in One and Two Dimensions*, Oxford Univ. Press, Oxford (1987); Cavanagh et al, *Protein NMR Spectroscopy*, Academic Press: San Diego (2007), which are hereby incorporated by reference in their entirety). The latter experiment represents a particularly attractive choice in cases where long proton $T_1$-relaxation times require long relaxation delays between scans in order to prevent that $^1$H-$^1$H NOE intensities are affected by largely varying individual $^1$H steady state magnetizations. For example, 2D [$^1$H,$^1$H] NOESY for structure determination of RNA is usually acquired with 5-10 seconds delay between scans (Varani et al., *Prog. Nucl. Magn. Reson. Spectrosc.*, 29:51-127 (1996); Szyperski et al., *J. Biomol. NMR*, 13:343-355 (1999); Hantz et al., *Int. J. Biol. Macromol.*, 28:273-284 (2001), which are hereby incorporated by reference in their entirety). If a PFG is applied during the mixing time of 2D [$^1$H,$^1$H] NOESY, the phases $\Phi_1$, $\Phi_2$, and $\Phi_3$ of the three $^1$H radiofrequency pulses and the receiver phase $\Phi_{Rec}$, are conventionally cycled for axial peak suppression as (Braun et al., *150 and More Basic NMR Experiments*; Wiley-VCH: Weinheim, Germany, (1998), which is hereby incorporated by reference in its entirety) ($\Phi_1$=0°,180°; $\Phi_2$=0°,0°; $\Phi_3$=0°,0°; $\Phi_{Rec}$=0°,180°). The corresponding SC NMR phase cycle for two-fold increased data acquisition speed then needs to be ($\Phi_1$=0°,0°; $\Phi_2$=0°,180°; $\Phi_3$=0°,180°; $\Phi_{Rec}$=0°,0°) in order to keep the receiver phase constant.

Third, hetero-nuclear SC NMR experiments can be devised considering that (i) the number of selective $^1$H radiofrequency pulses need to be kept minimal, (ii) an even number of π radiofrequency pulses can be applied non-selectively since $^1$H magnetization is then flipped back along z, and (iii) radiofrequency pulses on other spins which are not cycled can be applied non-selectively as long as the polarization transfer starts and ends on protons. An example for such a hetero-nuclear SC NMR experiment would be a hetero-nuclear multiple-quantum correlation (HMQC) experiment (Cavanagh et al., *Protein NMR Spectroscopy*, Academic Press: San Diego (2007), which is hereby incorporated by reference in its entirety), which relies on only two $^1$H and two $^{15}$N radiofrequency pulses. Conventionally (Cavanagh et al., *Protein NMR Spectroscopy*, Academic Press: San Diego (2007), which is hereby incorporated by reference in its entirety), the minimal phase cycle involves phase $\Phi_1$ of the first $^{15}$N radiofrequency pulse and the receiver phase $\Phi_{Rec}$, that is, ($\Phi_1$=0°, 180°; $\Phi_{Rec}$=0°,180°). The corresponding SC NMR phase cycle for two-fold increased data acquisition speed needs to cycle $\Phi_1$ along with the phase $\Phi_2$ of the first $^1$H radiofrequency pulse instead (i.e., $\Phi_1$=0°,180°; $\Phi_2$=0°,180°; $\Phi_{Rec}$=0°,0°) in order to keep the receiver phase constant.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for simultaneously conducting multiple steps of a cycle of a nuclear magnetic resonance (NMR) experiment without applying pulsed magnetic field gradients during signal acquisition comprising:

providing a sample;

designing the cycle so that a receiver phase for each step of the cycle of the NMR experiment is the same;

applying one or more spatially selective radiofrequency pulses to the sample under conditions effective to simultaneously spatially distribute radiofrequency power associated with each of the cycle steps to a plurality of spatially discrete sections within the sample such that each section executes an individual step of the cycle and resultant NMR signals from each of the cycle steps are produced simultaneously; and acquiring the NMR signals generated from said applying without applying pulsed magnetic field gradients.

2. The method according to claim 1, wherein the one or more spatially selective radiofrequency pulses comprise a composite radiofrequency pulse applied concurrently with a pulsed magnetic field gradient.

3. The method according to claim 2, wherein the composite radiofrequency pulse comprises a plurality of component radiofrequency pulses which individually excite distinct sections within the sample.

4. The method according to claim 3, wherein applying comprises modulating temporal extent, phase, or total power of each component radiofrequency pulse under conditions effective to vary spatial extent, phase, or flip angle of each section.

5. The method according to claim 1, wherein the spatial extent of each said discrete spatial section is adjusted to weight the signal from each of said experiment cycle steps.

6. The method according to claim 1, wherein the plurality of spatially discrete sections comprise a first fraction of a total sample volume and further comprising executing the method according to claim 1 on one or more other fractions of the total sample volume during spin relaxation delay of the first fraction.

7. The method according to claim 6, wherein the method is used to achieve quadrature detection in the indirect dimension of a multidimensional NMR experiment in a single transient.

8. The method according to claim 6, wherein the method is used to obtain multiple sub-spectra of a G-matrix Fourier transformation (GFT) NMR experiment.

9. The method according to claim 1, wherein the cycle of the NMR experiment is a radiofrequency pulse flip angle cycle and applying comprises applying one or more composite radiofrequency pulses simultaneously with a pulsed magnetic field gradient to the sample, wherein each section of the sample is selectively affected by a portion of the one or more composite radiofrequency pulses with an independent combination of flip angle and phase.

10. The method according to claim 1, wherein the cycle of the NMR experiment is a radiofrequency pulse phase cycle and applying comprises applying one or more composite radiofrequency pulses simultaneously with a pulsed magnetic field gradient to the sample, wherein each section of the sample is selectively affected by a portion of the one or more composite radiofrequency pulses with an independent phase.

11. The method according to claim 1, wherein the cycle of the NMR experiment is a pulsed magnetic field gradient strength cycle and applying comprises applying one or more composite radiofrequency pulses simultaneously with a pulsed magnetic field gradient to the sample, wherein each section of the sample selectively experiences an independent effective pulsed magnetic field gradient strength.

12. The method according to claim 1, wherein the method is used to achieve coherence selection in a multidimensional NMR experiment in a single transient.

13. The method according to claim 12, wherein coherence selection is used for obtaining multiple-quantum filtered correlation spectrum.

14. The method according to claim 13, wherein the NMR experiment is 2D [$^1$H,$^1$H]-Exclusive COSY (E.COSY).

15. The method according to claim 12, wherein coherence selection is used for obtaining multiple-quantum correlation spectrum.

16. The method according to claim 12, wherein coherence selection is used for obtaining heteronuclear correlation spectrum.

17. The method according to claim 1, wherein said method is used to obtain a sub-spectrum of a G-matrix Fourier transformation (GFT) NMR experiment from a single transient.

18. The method according to claim 1, wherein said method is used to suppress spectral artifacts.

19. The method according to claim 18, wherein the spectral artifacts arise from incomplete suppression of NMR signals of a solvent in the sample.

20. The method according to claim 18, wherein the spectral artifacts arise from NMR polarization giving rise to axial peaks.

* * * * *